United States Patent [19]

Rosner

[11] Patent Number: 4,678,460
[45] Date of Patent: Jul. 7, 1987

[54] PORTABLE RAPID MASSIVE PARENTERAL FLUID WARMING AND INFUSION APPARATUS

[76] Inventor: Mark S. Rosner, 27400 Franklin, Apt. #821, Southfield, Mich. 48034

[21] Appl. No.: 700,389

[22] Filed: Feb. 11, 1985

[51] Int. Cl.$^4$ .............................................. A61M 5/00
[52] U.S. Cl. ...................................... 604/113; 604/80; 604/83; 128/401
[58] Field of Search ...................... 604/113, 80, 83, 4, 604/29; 128/399, 400, 401; 219/302, 308

[56] References Cited

U.S. PATENT DOCUMENTS

| | | | |
|---|---|---|---|
| 3,103,928 | 9/1963 | Broman . | |
| 3,407,748 | 10/1968 | Mamo . | |
| 3,551,641 | 12/1970 | Truhan | 219/302 |
| 3,614,385 | 10/1971 | Horstmann | 219/302 |
| 3,629,552 | 12/1971 | Edging . | |
| 4,019,020 | 4/1977 | Bilbee et al. | 604/113 |
| 4,191,183 | 3/1980 | Mendelson | 604/83 |
| 4,345,919 | 8/1982 | Wilkinson et al. . | |
| 4,364,383 | 12/1982 | Vcelka | 604/250 |
| 4,507,116 | 3/1985 | Leibinsohn | 604/142 |
| 4,531,941 | 7/1985 | Zasuwa | 604/113 |
| 4,532,414 | 7/1985 | Shah et al. | 219/302 |

Primary Examiner—Stephen C. Pellegrino
Assistant Examiner—John D. Ferros
Attorney, Agent, or Firm—Cullen, Sloman, Cantor, Grauer, Scott and Rutherford

[57] ABSTRACT

A self contained portable apparatus for the rapid warming and infusion of massive amounts of a parenteral fluid into a patient under conditions where time is of the essence. The apparatus comprises a portable cabinet, a parenteral fluid supply system, a fluid warming system, and apparatus monitoring and failure warning systems. The portable cabinet has a rectangular shaped enclosure which houses portions of the fluid supply and warming systems and the monitoring and failure warning systems. Extending upwardly from the top of the rectangular enclosure is a vertical support member which carries upper and lower horizontal crossmembers. The upper crossmember carries a plurality of disposable parenteral fluid bags and their respective pressure cuffs which surround the bags. Serially connected to the fluid bags are, drip chambers for monitoring the flow of each fluid bag, a confluence chamber for combining the separate flows from the drip chambers into a unitary flow, a portion of a warm water heat exchanger for raising the temperature of the parenteral fluid, a filter for removing foreign particles and other debris from the parenteral fluid, and a bubble trap and eliminator for removing air from the parenteral fluid. The portion of the fluid supply system through which the parenteral fluid flows is disposable and may be supplied assembled and precharged to reduce the time for placing the apparatus in use. The fluid warming system in a dual heat system, having a primary heating element for maintaining the apparatus in a stand-by condition when the apparatus is not in use and a secondary heating element for raising the temperature of the parenteral fluid to the desired temperature while the apparatus is in use. Unique quick connect/disconnect means are provided for replacing the filter during the resuscitation of a patient and coupling the water side of the heat exchanger to the apparatus. Means are provided for simulating failure of the parenteral fluid supply and warming systems to test the condition of the systems.

34 Claims, 33 Drawing Figures

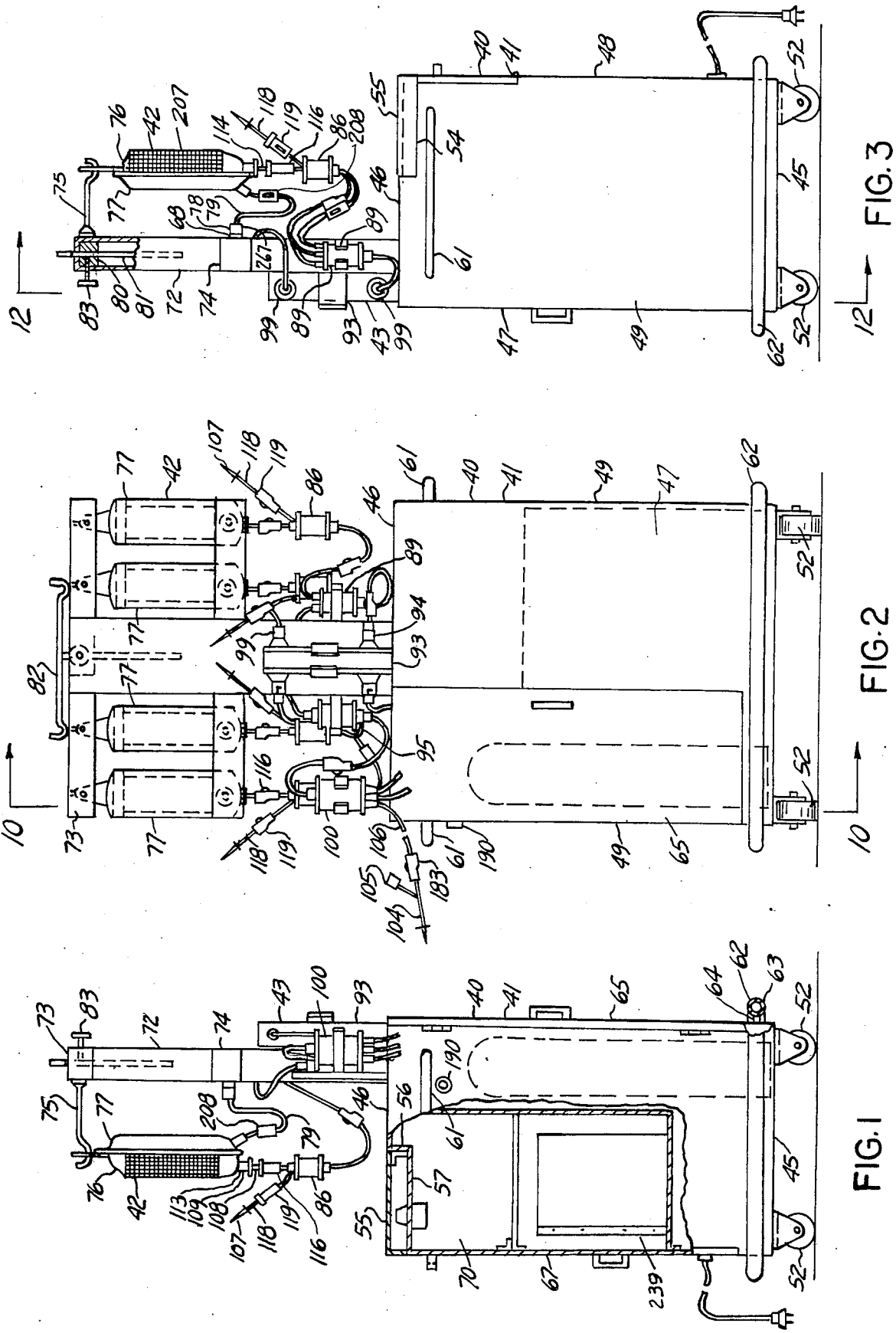

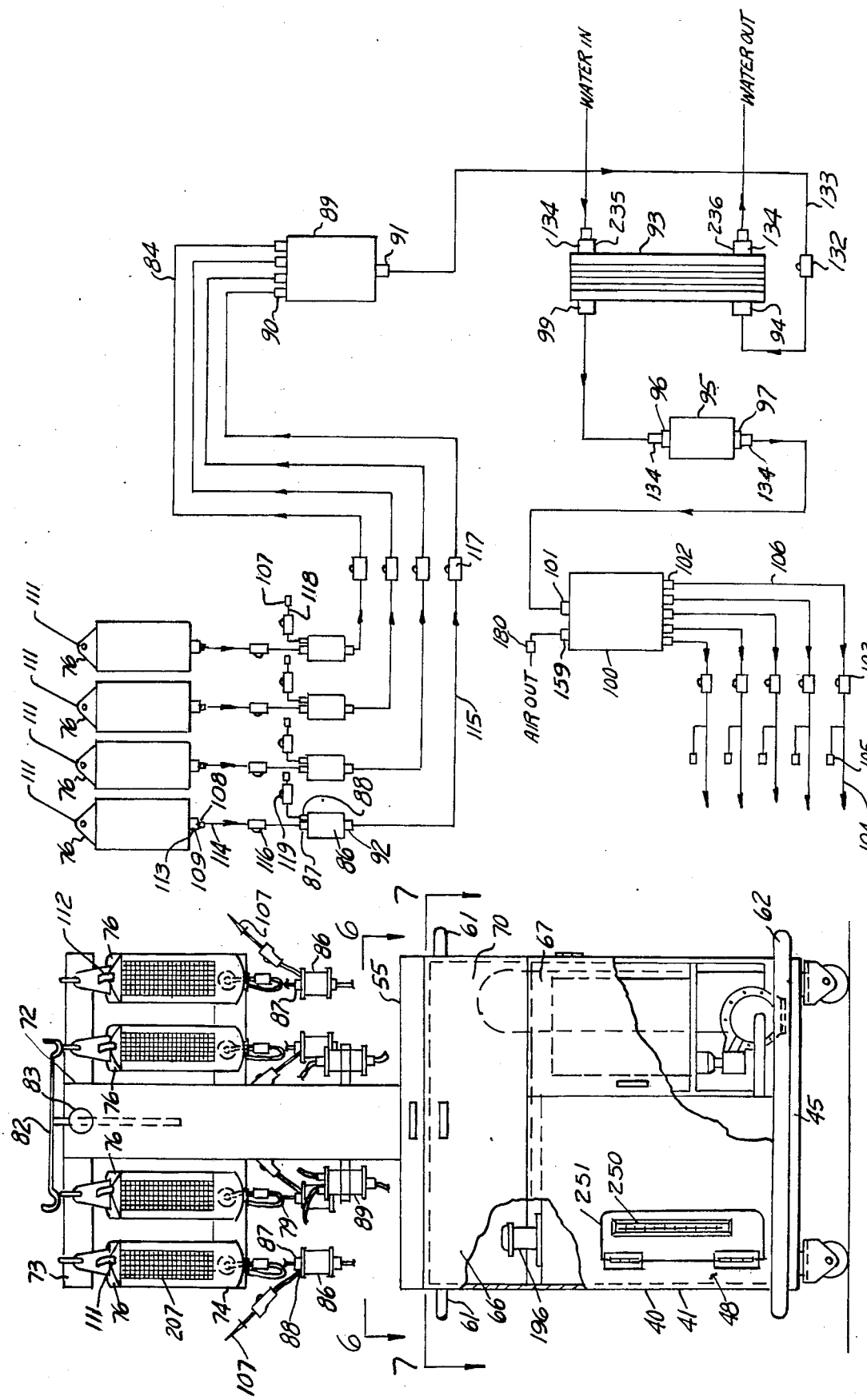

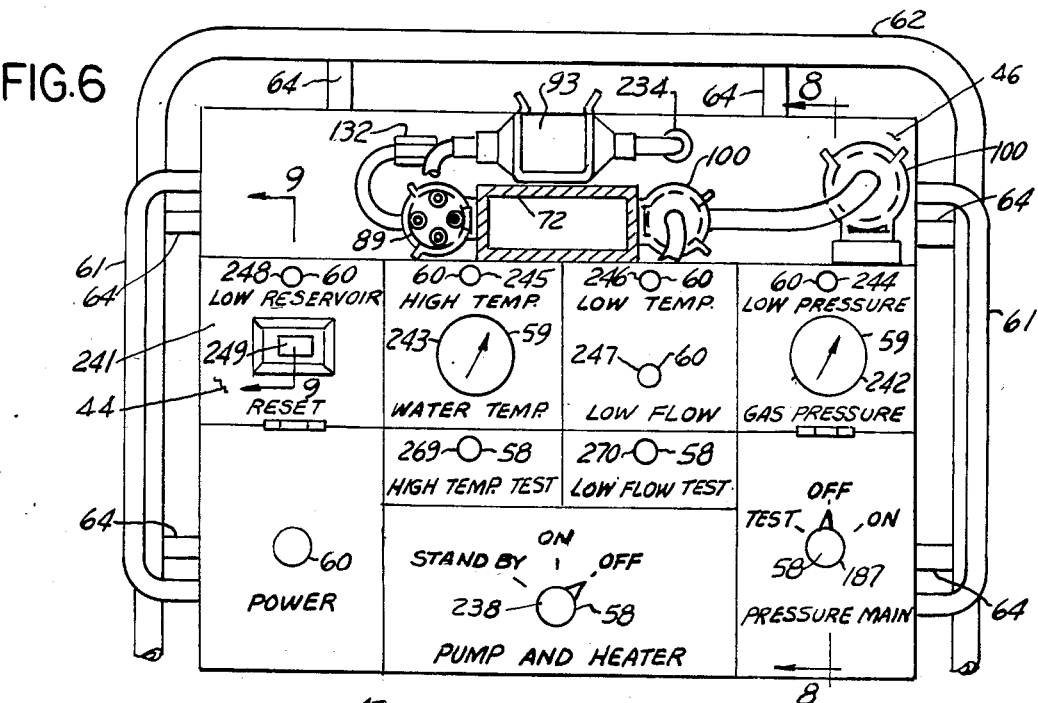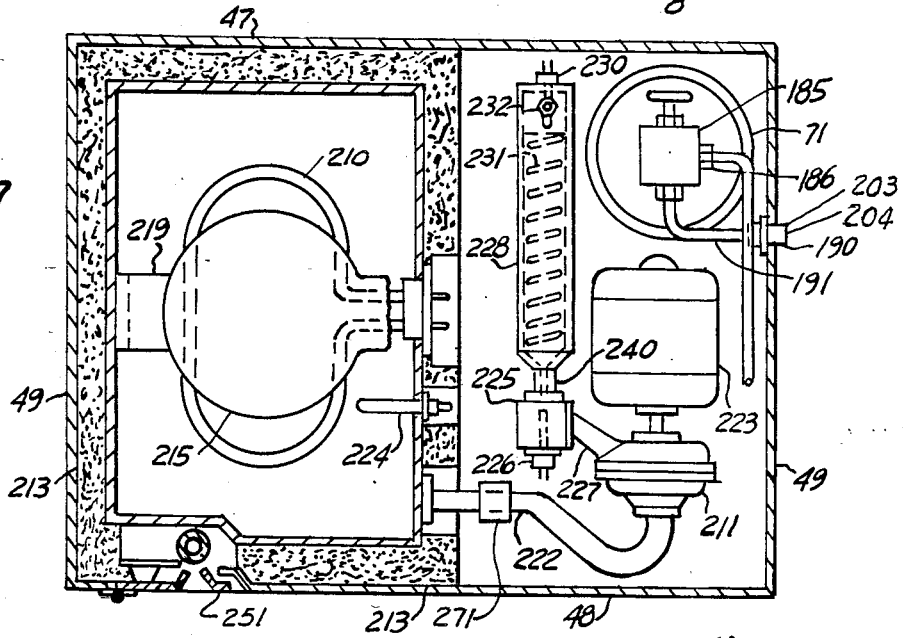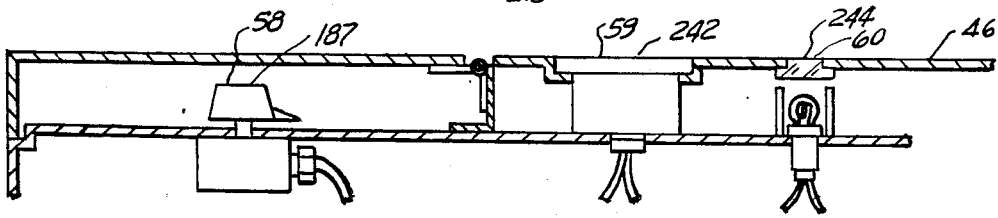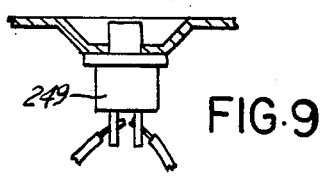

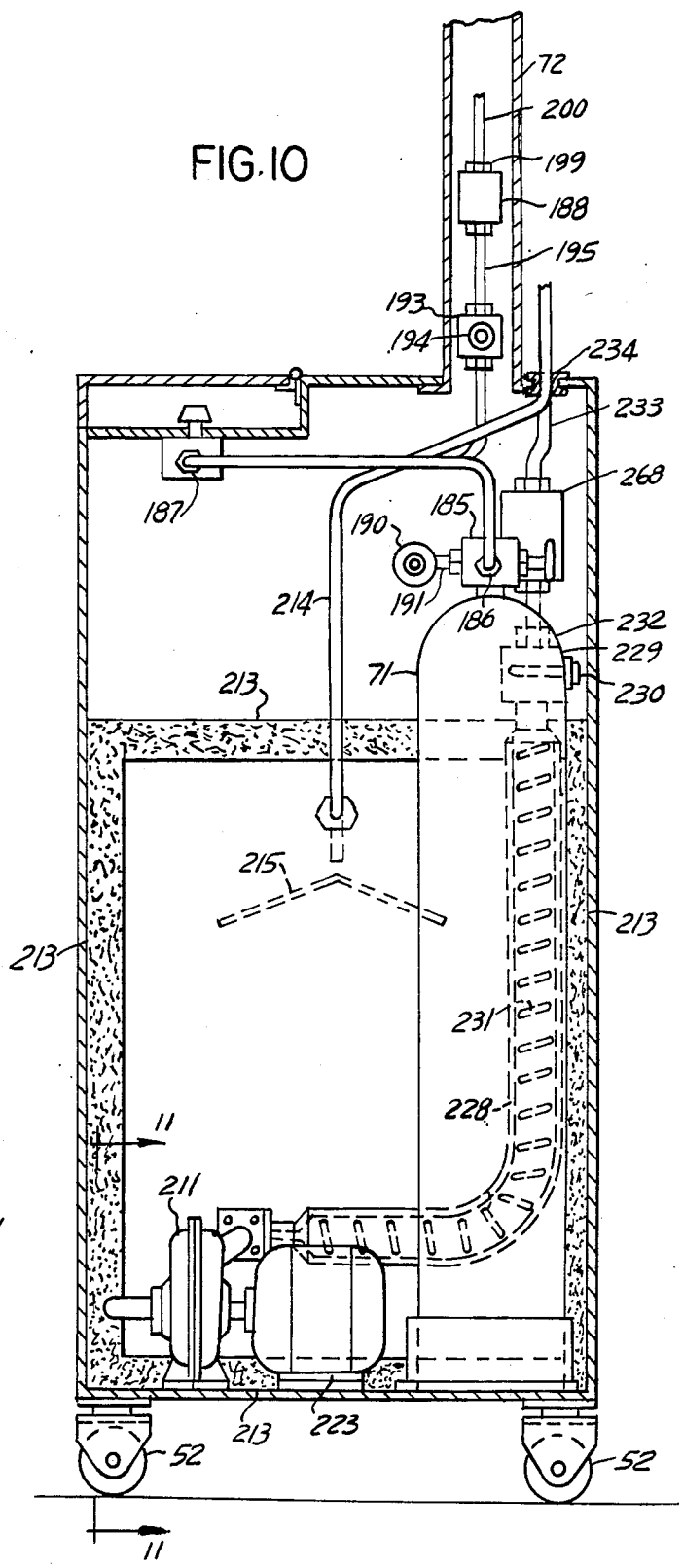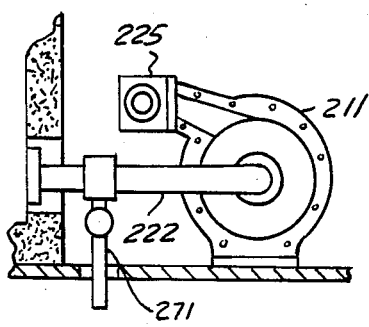

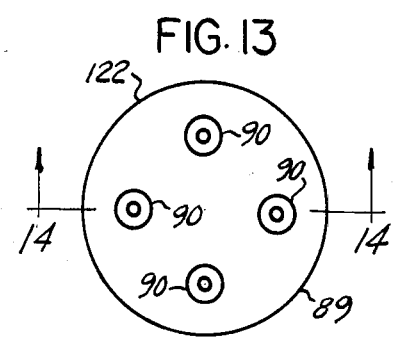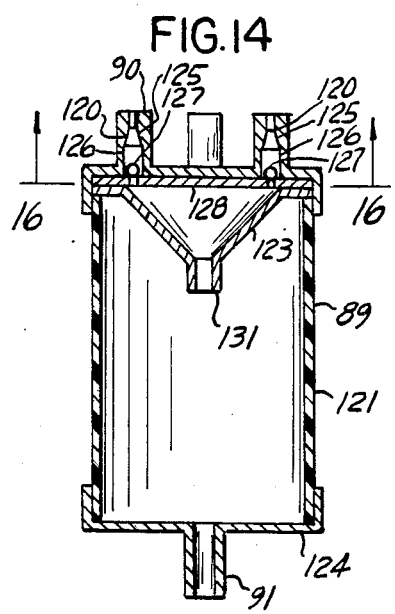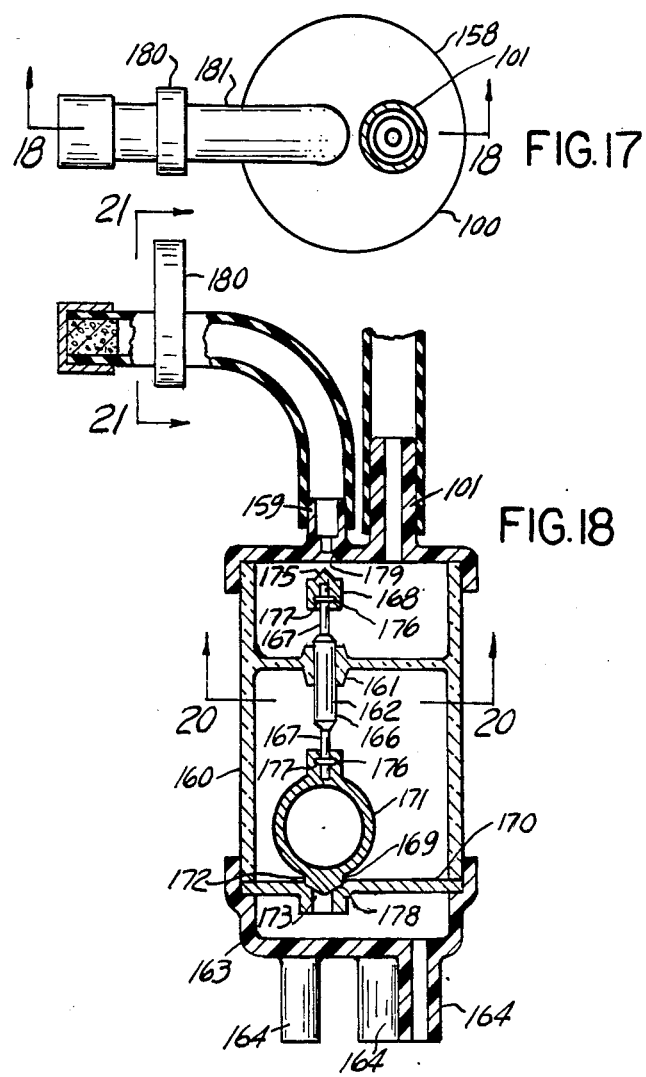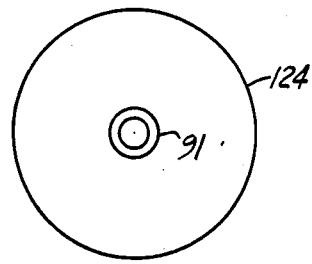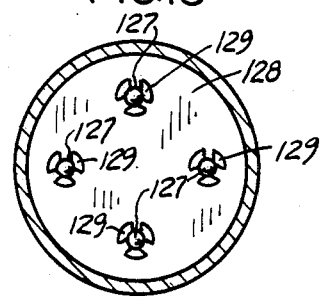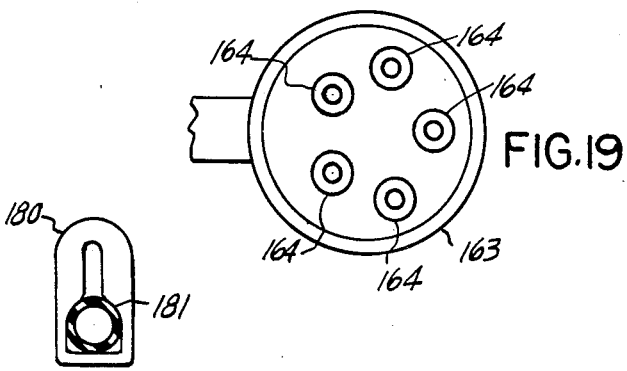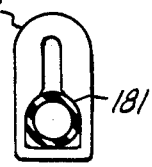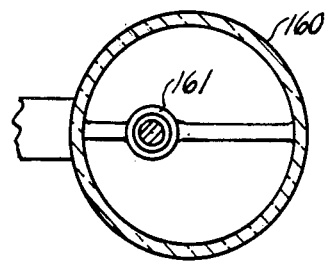

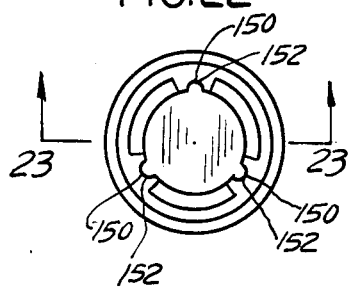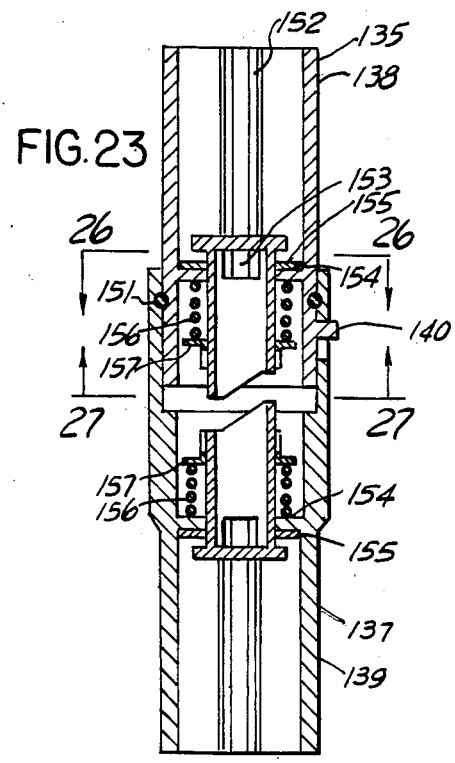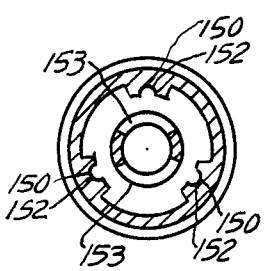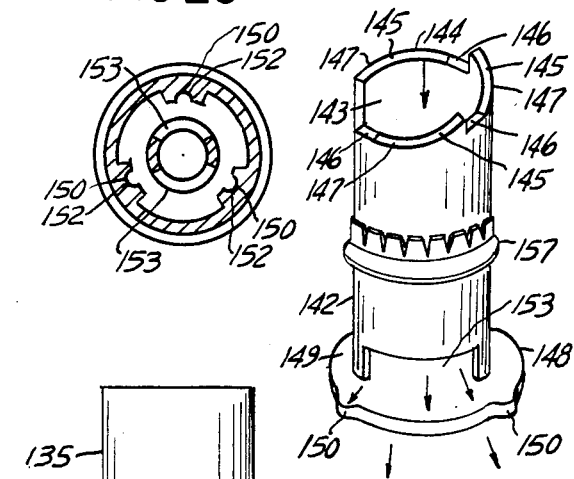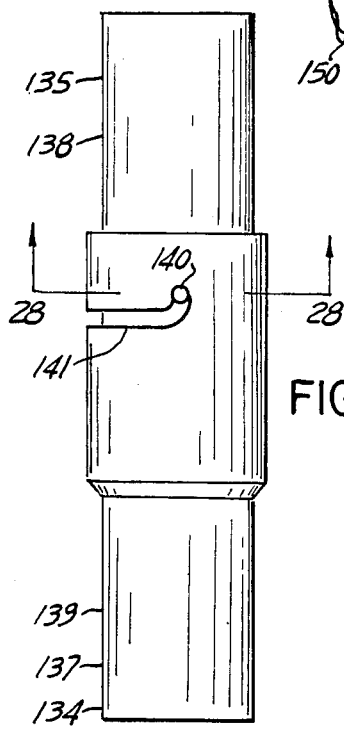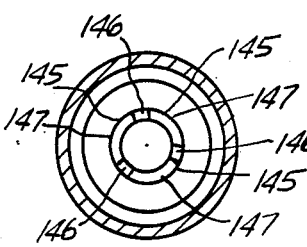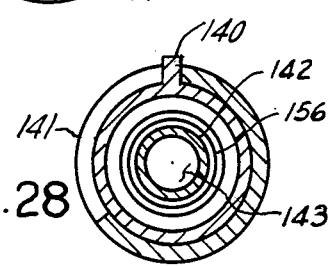

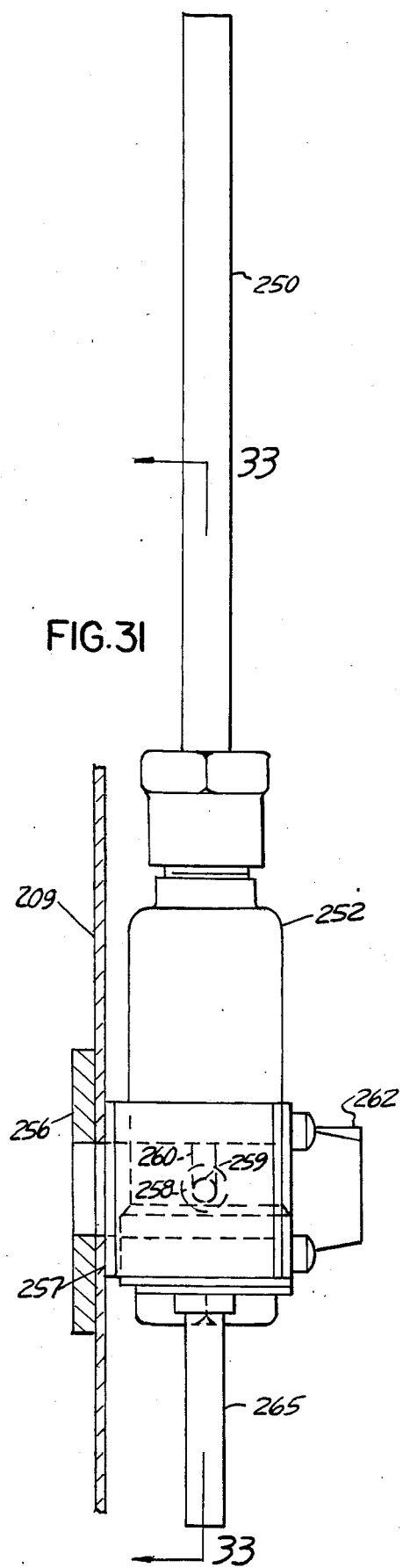
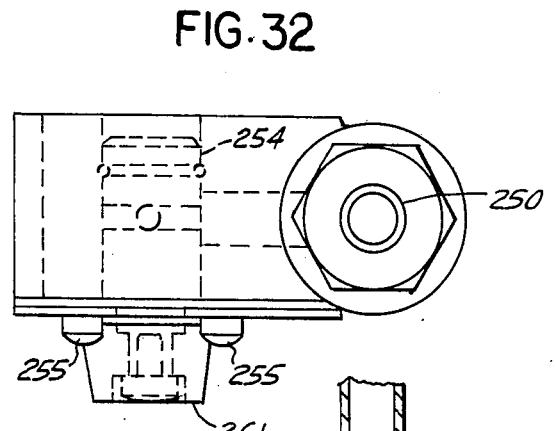
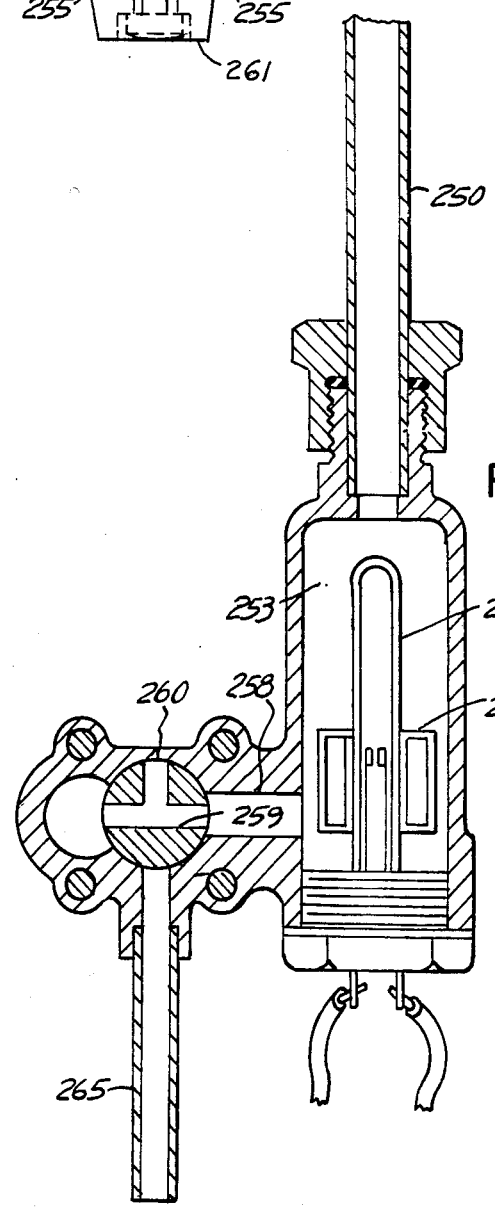

PORTABLE RAPID MASSIVE PARENTERAL FLUID WARMING AND INFUSION APPARATUS

BACKGROUND OF THE INVENTION

1. Field of the Invention

This invention relates to parenteral fluid warming and delivery equipment and more particularly to a portable apparatus for the rapid, massive warming and infusion into patients during trauma, surgery and other massive blood loss situations of cold banked blood and other unwarmed parenteral fluids for purposes of massive fluid resuscitation.

2. Description of Related Art

Massive infusion of parenteral fluids is the only means for restoring blood losses caused by acute severe hemorrhaging during surgery, trauma and other conditions, such as gastrointestinal bleeding, obstetric and gynecologic bleeding, rupture of arterial aneurysms, etc. Parenteral fluids administered during infusions include whole blood, packed red blood cells, plasma or albumin, and plasma and hemoglobin substitutes. Blood and blood products are generally withdrawn from refrigerated banks where blood is stored at four to six degrees centigrade to preserve the blood and prohibit growth of toxic organisms. Plasma substitutes, such as normal saline or lactated Ringer's solution, are usually stored at room temperature (18–20 degrees centigrade). When massive infusions are needed, it is crucial to infuse the fluids at the greatest possible flow rate.

Boyan, P.C. in *Cold or Warm Blood for Massive Transfusions*, Annals of Surgery (March, 1963) reported 12 cases of cardiac arrest in 25 patients infused with 3000 ml. or more of unwarmed refrigerated cold banked blood at a rate of 50 ml. or more per minute, as compared to only 8 cases of cardiac arrest in 118 patients infused at the same rate with pre-warmed blood. The occurrence of cardiac dysfunction in patients infused with unwarmed banked refrigerated blood increased still further to 21 out of 36 patients when 6,000 ml. or more of blood was administered at a rate of 100 ml. or more per minute.

As summarized by Boyan, deleterious effects of massive hemorrhaging include vaso-constriction, reduction of cardiac output, blood pressure and coronary flow with subsequent myocardial depression, inadequate brain and other organ and tissue perfusion and changes in the acid-base balance in the direction of metabolic acidosis, which if not corrected progress to an irreversible state until death inevitably occurs.

Collins J. A. in *Preservation of Red Blood Cells*, National Academy of Sciences (June, 1972) reported that during the Vietnam war the need to transfuse blood as rapidly as possible "severely reduced the use of packed red cells . . . because of the frustratingly high viscosity and consequent slow flow during transfusion." Although it has been known for some time that warming packed red blood cells decreases its viscosity and thereby increases its flow during a transfusion, available equipment for accomplishing this end has been grossly inadequate.

Russell, W. J. in *A Discussion of the Problems of Heat Exchange Blood Warming Devices*, British Journal of Anesthesia, Vol. 41, page 345, (1969) reported that the viscosity of blood changes about 2.5 times as it is warmed from 0 to 37 degrees centigrade. Since pressure losses increase directly with viscosity, it will be appreciated that higher driving pressures are required to administer blood which has been withdrawn from refrigerated banks without warming.

Heretofore, blood warming and delivery systems have consisted of non-standardized arrangements of heat exchanger units and conventional blood delivery disposables. Present state of the art blood warming machines/systems accomplish blood warming by one of several methods. One is a dry heat system, where heat is transferred from a metal plate through a disposable plastic bag containing the parenteral fluid. Another method involves immersion of a coil of IV tubing into a warm water bath with the heat transferring through the walls of the IV tubing.

The blood warmer used by Boyan (representative of coil blood warmers) consisted of 24 ft. of coiled 4.5 mm. plastic tubing immersed in a 20 ml. water bath and maintained at a 37 degree temperature by adding warm water to the immersion bath. Boyan reported that the apparatus had a capability of raising the temperature of cold banked blood from 4–5.8 degrees to 30–36 degrees within a range of transfusion rates of 50–150 ml. per minute.

In a recent survey of medical blood warmers, (see *Blood Warmers*, ECRI publication Health Devices, July, 1984), out of five warmers tested, the highest rated warmer was rated overall as only conditionally acceptable. Of further significance is that only one of the five units was considered to have adequate warm-up capability, none met the ECRI minimum output temperature criteria of 32 degrees centigrade for all flow rates, test results did not meet manufacturers' specifications and the maximum measured flow rate through disposables of the five warmers was 151 ml./min. at a pressure of 300 mm. Hg.

In addition to the above, other negative characteristics observed in five blood warmers include overheating during malfunctions, poor and inadequate capabilities for testing failure warning systems, poor temperature regulation, inadequate warning of system malfunction and inadequate display of important system operating parameters.

Current non-standardized practices in blood warming and delivery equipment are susceptible to mishaps and undesirable delays when setting up and operating the equipment during emergency and surgical conditions and make the equipment undesirable and inefficient to use.

By way of example, with current equipment, parental fluid bags are pressurized by inflating surrounding flexible infuser cuffs with hand pumps to increase the rate of fluid flow. Over the course of several minutes the pressure in an infuser cuff is depleted and it becomes necessary to again pump up the infuser cuff to restore parenteral fluid flow. If three or four fluid bags are used, separate infuser cuffs and hand pumps are required and it becomes extremely difficult for one person to simultaneously monitor the fluid level of each bag while simultaneously operating hand pumps to maintain infuser cuff pressures and replacing empty bags. Thus, with current equipment two or three nursing personnel are generally needed to operate the fluid delivery equipment during resuscitation of a severely hypovolemic individual.

Furthermore, because of the small vent which is provided in each of the hand pumps for deflating the pressure infuser cuffs, over 30 seconds is typically required for deflating an infuser cuff to release and replace a bag.

Still further, IV poles with bags carried thereon may be positioned on all sides of a patient resulting in a maze of crossing IV lines routed to the patient's right side, left side and the patient's groin. Because of the lack of organization and in particular centralization, bags are sometimes reversed whereby fluid level cannot be conveniently observed. Also, origin and insertion points of IV lines are not obvious, resulting in time consuming delays in monitoring flow in IV lines as well as identifying IV lines for drug administration.

Still further, in the resuscitation room bags carried on IV poles for immediate use are frequently pre-assembled with standard IV tubing. Therefore, when blood is needed the standard IV tubing must be replaced with special blood administering tubing to provide double inlet ports and an in-line filter, all of which are not present in the standard tubing. This is difficult because IV lines, which are generally secured by tape to a patient, are not readily accessible so that they can be quickly detached from the patient. Thus, when it is necessary to change to blood tubing, tape must be removed and the substituted blood tubing taped in place, a time consuming process.

Still further, with existing equipment it is necessary to use a separate blood warmer with each IV line involved in blood transfusion, adding to the cost and complexity of the equipment.

Still further, since current blood warmers inadequately warm blood and parenteral fluids, and markedly retard flow rate, they are frequently not used, thereby resulting in parenteral fluid resuscitation without the benefits of warming.

Still further, with existing blood warming and delivery equipment, it is not uncommon to introduce small amounts of air into a patient because of the lack of a bubble trap and eliminator.

With the foregoing in mind, a portable apparatus for the rapid and massive warming and infusion of parenteral fluids would fill recognized medical needs and advance the art of parenteral fluid infusion.

SUMMARY OF THE INVENTION

The present invention is directed to a portable apparatus for the rapid restoration of blood losses caused by acute severe hemorrhaging. The portable parenteral fluid warming and massive delivery apparatus embodying the invention generally comprises a portable cabinet, a pressurized disposable parenteral fluid supply system, a parenteral fluid warming system, and monitoring and failure warning systems.

Two important benefits of the present invention are: (1) hypothermic potential is reduced in patients requiring large amounts of transfused fluids by the infusion of warmed parenteral fluids, and (2) mortality of patients requiring large amounts of transfused fluids is reduced by immediate rapid delivery of massive amounts of parenteral fluids.

The compact portable cabinet is generally of rectangular shape and carried on casters which swivel to maximize the mobility of the apparatus and facilitate its movement in and out of small spaces in resuscitation and operating rooms. The interior of the cabinet includes storage space and houses portions of the parenteral fluid supply and warming systems.

The rear outermost upper portion of the cabinet is stepped and the stepped portions enclosed by a pivotally mounted transparent L-shaped cover. Beneath the L-shaped cover are mounted selected test and "on/off" controls. On the countertop of the cabinet is a control panel having indicator lights and gauges for monitoring the performance of the individual systems.

At the forward upper portion of the cabinet is an upward extending vertical stanchion which carries an upper horizontal crossmember and a lower horizontal crossmember, both crossmembers being fixedly attached to the vertical stanchion. A plurality of outwardly projecting slender rod hook members are attached to the upper crossmember and support a plurality of disposable parenteral fluid bags and their respective surrounding expansible pressure infusor cuffs.

A telescoping T-shaped auxiliary IV pole is adjustably clamped to the upper end portion of the vertical stanchion for mounting bags or bottles containing medications and other fluids, or parenteral fluid bags, should the pressure infuser system fail.

The parenteral fluid supply system has a disposable fluid flow circuit for delivering and infusing a parenteral fluid into a patient and a fluid pressure circuit for rapidly infusing massive amounts of the fluid into the patient. The flexible parenteral fluid bags are serially connected to a fluid network consisting of drip chambers, a confluence chamber, one portion of a heat exchanger, a blood filter, a bubble trap, and a network of interconnecting flexible tubular lines, said lines being adapted to connect one or more catheters at the distal ends thereof for infusing the parenteral fluid into a patient. A plurality of roller clamps engaging the lines control the flow rate of fluid therein.

All members of the fluid flow system, including the IV parenteral fluid bags, drip chambers, confluence chamber, heat exchanger, bubble trap, filter chambers and inter-connecting tubing are disposable and intended to be only used for one patient since no efficient or effective way is known for sterilizing these units after use.

It is a primary object of the present invention to provide a simple, compact and highly effective portable parenteral fluid warming and delivery apparatus for rapidly administering massive amounts of warm blood and other parenteral fluids to a patient suffering from massive blood loss during conditions such as surgery and trauma.

It is another object in addition to the foregoing objects to provide in a parenteral fluid apparatus easy distal access for administering medications and conducting central venous pressure measurements.

It is another object in addition to the foregoing object to increase the rate of infusion of parenteral fluids during emergency conditions such as acute hemorrhaging.

It is another object in addition to the foregoing objects to prevent the occurrence of air embolisms during the admistration of parenteral fluids.

It is another object in addition to the foregoing objects to provide a centralized arrangement of IV bags and attaching lines and equipment for the administration of IV fluids by a single individual.

It is another object in addition to the foregoing objects to provide a highly accurate means of temperature regulation in a parenteral fluid warming apparatus.

It is another object in addition to the foregoing objects to provide a portable parenteral fluid warming and delivery apparatus which is instantly available for administering warm blood and other parenteral fluids to a patient.

It is another object in addition to the foregoing objects to provide in a portable parenteral fluid warming and delivery apparatus a malfunction warning system which can be tested by simulations of actual failures.

It is another object in addition to the foregoing objects to provide a portable parenteral fluid apparatus capable of administering greater quantities of parenteral fluids at normal body temperature and more rapidly than heretofore available.

It is another object in addition to the foregoing objects to provide a portable parenteral fluid warming and delivery apparatus which does not require a priming of the disposable parenteral fluid pathway.

It is another object in addition to the foregoing objects to provide in a portable parenteral fluid warming and delivery apparatus a level of reliability heretofore not available.

Other features, objects and benefits of the invention will become apparent from the ensuing description and accompanying drawings which disclose the invention in detail. A preferred embodiment is disclosed in accordance with the best mode contemplated in carrying out the invention and the subject matter in which exclusive property rights are claimed is set forth in each of the numbered claims at the conclusion of the detailed description.

BRIEF DESCRIPTION OF THE DRAWINGS

FIG. 1 is a right side elevational view of a portable massive parenteral fluid warming and infusion apparatus constructed in accordance with the present invention.

FIG. 2 is a front elevational view showing the apparatus as viewed from the patient's side.

FIG. 3 is a left side elevational view of the apparatus.

FIG. 4 is a rear elevational view of the apparatus showing the apparatus as viewed from the operator's side.

FIG. 5 is a block diagram of the parenteral fluid circuit of the apparatus.

FIG. 6 is a cross-sectional view taken on the line 6—6 of FIG. 4 showing gauges and controls on the countertop of the portable cabinet.

FIG. 7 is a cross-sectional view taken on the line 7—7 of FIG. 4 showing plan views of some components of the parenteral fluid warming and pressure infuser systems located inside the portable cabinet.

FIG. 8 is a cross-sectional view taken on the line 8—8 of FIG. 6 showing gauges and controls.

FIG. 9 is a cross-sectional view taken on the line 9—9 of FIG. 6 showing the failure warning system reset control of the apparatus.

FIG. 10 is a cross-sectional view taken on the line 10—10 of FIG. 2 showing right side elevational views of some components of the parenteral fluid warming and pressure infuser systems within the portable cabinet.

FIG. 11 is a partial cross-sectional view taken on the line 11—11 of FIG. 10 showing the rear elevational view of the water warming pump and reservoir drain.

FIG. 13 is a plan view of a confluence chamber.

FIG. 14 is a cross-sectional view taken on the line 14—14 of FIG. 13 showing the internal construction of the confluence chamber.

FIG. 15 is a bottom view of the confluence chamber.

FIG. 16 is a cross-sectional view taken on the line 16—16 of FIG. 14 showing the orifice plate of check valves of the confluence chamber.

FIG. 17 is a plan view of a bubble trap and eliminator.

FIG. 18 is a cross-sectional view taken on the line 18—18 of FIG. 17 showing the internal construction of the bubble trap and eliminator.

FIG. 19 is a bottom view of the bubble trap and eliminator.

FIG. 20 is a cross-sectional view taken on the line 20—20 of FIG. 18 showing the valve guide of the bubble trap and eliminator.

FIG. 21 is a cross-sectional view taken on the line 21—21 of FIG. 18 showing an elevational view of a pinch clamp.

FIG. 22 is a plan view of the quick connect/disconnect coupling.

FIG. 23 is a cross-sectional view taken on the line 23—23 of FIG. 22 showing the internal construction of the quick connect/disconnect coupling.

FIG. 24 is a bottom view of the quick connect/disconnect coupling.

FIG. 25 is a side elevational view of a quick connect/disconnect coupling.

FIG. 26 is a cross-sectional view taken on the line 26—26 of FIG. 23 showing the fenestrations of the coupling valve.

FIG. 27 is a cross-sectional view taken on the line 27—27 of FIG. 23 showing cusps on the end of the coupling valve.

FIG. 28 is a cross-sectional view taken on the line 28—28 of FIG. 25 showing the J-slot and lock pin of the quick connect/disconnect coupling.

FIG. 29 is an elevational view of the spring retainer of the quick connect/disconnect coupling.

FIG. 30 is an enlarged perspective view showing the valve and spring retainer of the quick connect/disconnect coupling.

FIG. 31 is a side elevational view of a water level gauge and low level warning indicator.

FIG. 32 is a plan view of the water level gauge and low level warning indicator.

FIG. 33 is a cross-sectional view taken on the line 33—33 of FIG. 31 showing the internal construction of the water level gauge and low level warning indicator.

DESCRIPTION OF THE PREFERRED EMBODIMENT

Figure 12:
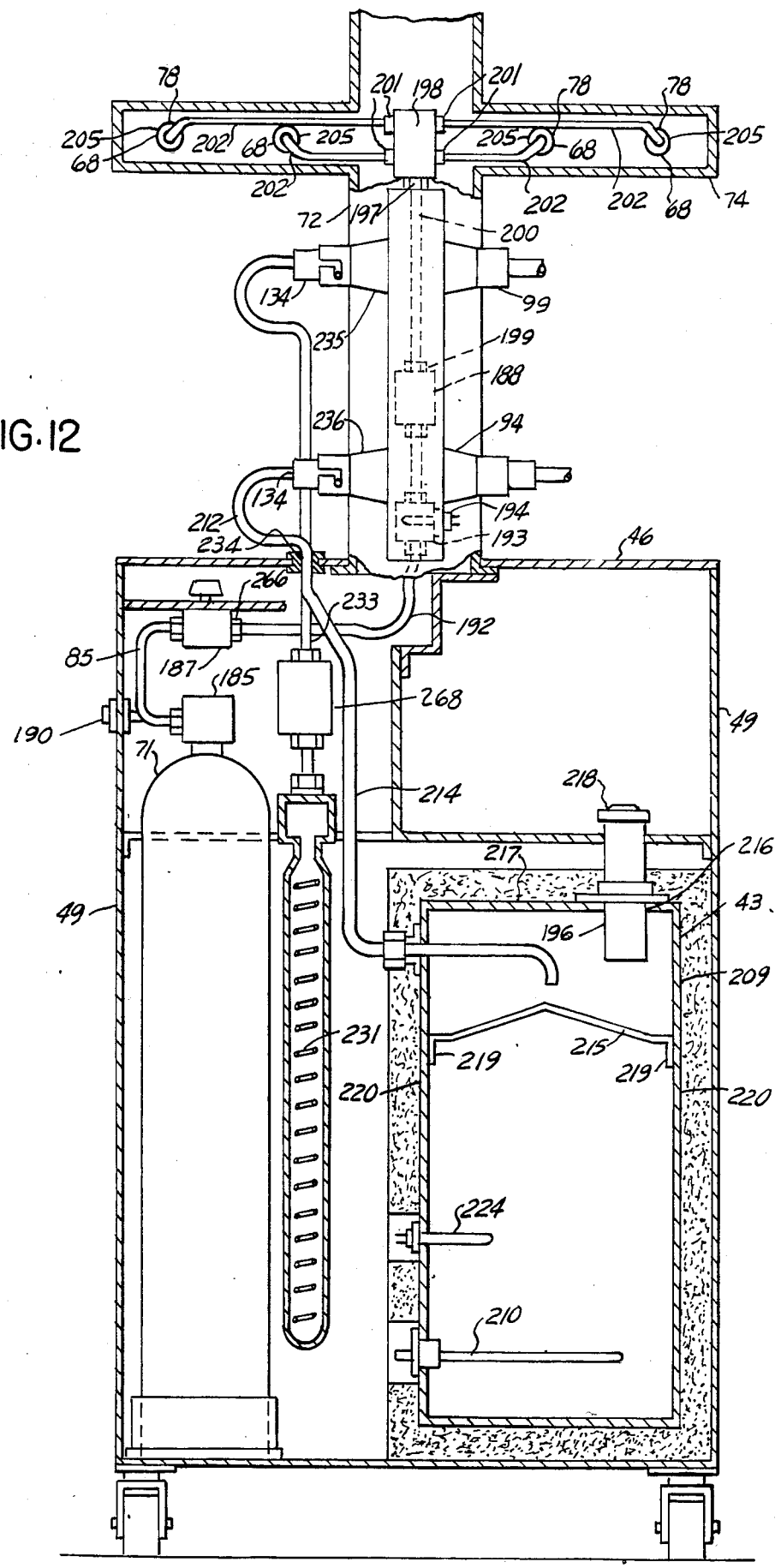
FIG. 12 is a cross-sectional view taken on the line 12—12 of FIG. 3 showing front elevational views of some components of the parenteral fluid warming and pressure infuser systems inside the portable cabinet.

Referring now to the drawings wherein like reference characters refer to like and corresponding parts throughout the several views, the portable parenteral fluid warming and massive delivery apparatus 40 embodying the invention disclosed in FIGS. 1 through 33, inclusive, comprises, in general, a portable cabinet 41, a pressurized disposable parenteral fluid supply system 42, a parenteral fluid warming system 43, and a monitoring and failure warning system 44.

THE PORTABLE CABINET

The portable cabinet 41, being of generally rectangular shape, has a lower wall 45, an upper wall 46 which serves as a countertop, a forward wall 47, a rearward wall 48 and a pair of side walls 49. During service, the apparatus 40 is positioned adjacent to a patient's bed and oriented with the forward cabinet wall 47 facing the patient and the cabinet rearward wall 48 facing an operator. The cabinet 41 is carried on conventional casters 52 fixed to the lower corners of the cabinet 41. The casters 52 preferably swivel to maximize mobility and facilitate moving the apparatus 40 in and out of the usual small spaces of resuscitation and operating rooms.

The cabinet 41 is compact with overall dimensions of about 18 inches wide, about 14 inches deep, and about 60 to 65 inches high measured to the top of an upper crossmember 73. The corresponding height of the countertop 46 is about 30 to 32 inches. Compactness is a desirable feature because of space limitations in resuscitation and operating rooms.

The outermost upper portion of the cabinet 41, on the operator's side, is stepped and enclosed by a transparent L-shaped cover 55 pivotally mounted at the forward portion thereof. The stepped cabinet portion 54 has a forward vertical wall 56 and an adjoining lower horizontal wall 57. A group of test and "on/off" controls, hereinafter described, are mounted beneath the L-cover 55 on the lower horizontal wall 57 to prevent damage, tampering or accidental actuation of the controls 58 at inappropriate times.

Mounted ahead of the stepped portion 54 on the uppermost wall 46 of said cabinet 41 are gauges 59 and indicator lights 60, hereinafter described, which monitor the performance of the parenteral fluid warming 43 and delivery 42 systems and indicate the source of an equipment malfunction. The uppermost portions of the transparent L-cover 55 and the countertop mounted gauges 59 are flush with the countertop surface 46 whereby the entire countertop is flat and usable for holding medications and miscellaneous equipment during patient resuscitation.

Fixedly attached at the upper portion of each side wall 49 of the cabinet 41 is a U-shaped handle 61, for pushing and steering the apparatus 40 in the resuscitation and operating rooms or to other locations. A bumper rail 62 completely encircles the lower portion of the cabinet 41 to prevent damaging the cabinet 41 by impacts with wall railings or other objects. The rail 62, spaced outwardly from the outer walls of the cabinet 41, is preferably covered with a compliant rubber-like material 63 and is affixed to the cabinet walls by struts 64 or other suitable means.

The front 47 and rear 48 cabinet walls are apertured and fitted with a forward door 65, an upper rear door 66 and a lower rear door 67 for access to a storage compartment 70 and electrical, pneumatic and mechanical components within the cabinet.

The pivotally mounted downward swinging upper rear door 66 covers the storage compartment 70 which is provided for storing spare components required to be replaced during resuscitation. The pivotally mounted outward swinging lower rear door 67 allows servicing of controls and components which are mounted within the cabinet 41. The front door 65 or patient's side of the cabinet 41 is a pivotally mounted outward swinging door 65 for servicing interior controls and components on the forward side and replacing a compressed gas cylinder 71 hereinafter described.

At the forward upper portion of the cabinet 41 a vertical upward extending generally rectangular shaped tubular support member 72 is fixedly attached which carries a tubular upper horizontal crossmember 73 and a tubular lower horizontal crossmember 74, both of said crossmembers 73, 74 being fixedly attached at the center portions thereof to the vertical support member 72.

Extending outwardly from the rear of the upper crossmember 73 are four slender rod-type hook members 75, the forward end portions of each said members 75 being fixedly attached to the rear wall of the upper crossmember 73. Each of the slender hook members 75 mounts and supports a disposable parenteral fluid bag 76 and a respective pressure infusor cuff 77, hereinafter described.

Mounted to the rear wall of the lower crossmember 74 are four members 78 of conventional quick connect-/disconnect couplings 68, hereinafter described, which connect one end portion of flexible pressure lines 79 from the pressure infuser cuffs 77 to the pressure delivery circuit 85 of the fluid supply system 42.

With reference to FIG. 4, the upper end portion of the vertical support member 72 has an aperture 80 in the center thereof which receives the lower vertical portion 81 of a T-shaped auxiliary IV pole 82, said vertical pole portion 81 being adjustably clamped to the vertical cabinet member 72 by a thumb screw 83 threadably engaging the rear portion of the vertical member 72. The auxiliary IV pole 82 is desirable for supporting bags or bottles (not shown) containing fluids and medications other than those parenteral fluids being infused under pressure during patient resuscitation. Also, in the event of failure of the pressure infuser system 85, parenteral fluid bags 76 can be supported from the auxiliary IV pole 82 and the parenteral fluid fed by gravity to a patient undergoing infusion.

PARENTERAL FLUID SUPPLY SYSTEM

The parenteral fluid supply system 42 consists of two separate circuits, namely, a disposable fluid flow circuit 84 for delivering a parenteral fluid to a patient and a pressure delivery circuit 85 for rapidly infusing massive quantities of the fluid into the patient.

DISPOSABLE FLUID FLOW CIRCUIT

The fluid flow circuit comprises four parenteral IV fluid bags 76 in a parallel flow arrangement serially connected to a fluid network comprised of a drip chamber 86 having one inlet port 87 serially connected to each of said flexible IV bags 76 and another inlet port 88 thereof used for adding normal saline to said parenteral fluids and a single outlet port 92; a confluence chamber 89 having multiple inlet ports 90 and a single outlet port 91, the inlet ports 90 thereof serially connected to corresponding outlet ports 92 of said drip chambers 86; one portion of a heat exchanger 93 having an inlet port 94 and an outlet port 99, the inlet port 94 thereof serially connected to the outlet port 91 of said confluence chamber 89; a filter 95 having single inlet 96 and outlet 97 ports, the inlet port 96 thereof serially connected to the outlet port 99 of said portion of the heat exchanger 93; a bubble trap and eliminator 100 having a single inlet port 101 and multiple outlet ports 102, the inlet port 101 thereof serially connected to the outlet port 97 of said filter 95; flexible tubular line means for interconnecting the components of said fluid network, each of said tubular line means being adapted to attach catheters (not shown) for infusing parenteral fluids from said flexible bags 76 into a patient; an injection port 105 for administering medications other than parenteral fluids operatively connected to each line segment 106 connected to the outlet ports 102 of said bubble trap and eliminator 100; and clamp means for controlling the flow rate of fluids therein.

All components of the fluid flow system, including the IV parenteral fluid bags 76, drip chambers 86, confluence chamber 89, heat exchanger 93, bubble trap and eliminator 100, filter chamber 95 and inter-connecting tubing are disposable and intended to be used for only one patient since there is no efficient or effective way of sterilizing the components after use.

In the current practice of administering parenteral fluids to patients during fluid resuscitation, IV bags with attached tubing are suspended from IV poles and the IV tubing attached to the bags are pre-filled with fluid from their respective bags. The disadvantage of this practice is that after pre-filling, the bags and IV tubing are deemed sterile for only 24 hours and must be afterwards discarded. The primary reason for discarding the bags and lines after this time period is that the IV bag and lines must be spiked during pre-filling of the lines which exposes the system to air borne bacteria.

One feature of the flow circuit 84 of the present invention 40 is that the entire flow circuit 84 may be optionally pre-charged at manufacture with a fluid, such as, a normal saline solution. The advantages of pre-charging over the prior art of spiking the IV bags 76 is that with pre-charging there is no necessity of purging air to prevent embolism prior to infusion as is the case with the prior art. An additional advantage is that contamination of the flow circuit 84, from exposure to air and bacteria, is avoided since there is no need to spike the IV bags 76.

Pre-charging the fluid network 84 with IV fluid also allows an immediate start-up of the apparatus 40 since to begin infusion of the parenteral fluid into a patient it is only necessary to insert the IV spikes 108 at the distal input ends of the fluid network 84 into the outlet ports 109 of the IV bags 76, release the appropriate roller clamps 116, 117, 132 and 183 and activate the electrical 238 and pressure 187 on/off controls. When administering massive infusions to a seriously ill patient during emergency life threatening situations, this time saving is invaluable.

Yet another feature of the fluid flow circuit 84 of the present invention is that low cost disposable quick connect/disconnect couplings 134 are provided for quickly and efficiently coupling the filter 95 into the fluid network 84. This feature shortens the time for replacement of the filter 95 during resuscitation as well as preventing air from entering the system 84 during replacement of the filter 95. Still yet another feature of the fluid flow circuit 84 is an efficient arrangement of circuit components which minimizes pressure losses, maximizes flow rate and reduces hemolysis during the use of whole blood or packed red cells.

Each parenteral fluid bag 76 is an existing type of transparent bag 76 which allows the operator to monitor the quantity of fluid in the bag 76. Each bag 76 has a filled volume of about 500 or 1000 cc. and is made of a flexible, squeezable material whereby most of the fluid can be discharged by squeezing the bag 76 at the sides thereof. The upper portion of the bag 76 is formed in the shape of a loop 111 which receives the strap portion 112 of a corresponding pressure infuser cuff 77 hereinafter described. At the lower end portion of each bag 76 is the downward extending female member 109 of the spike coupling 113 which serves as the outlet port 109 of the bag 76.

Before beginning resuscitation of a patient, fluid bags 76 scheduled for resuscitation are connected to the fluid network 84 by inserting the spikes 108 suitably attached to the segments 114 of flexible line forming the input ends of the fluid network 84 into the downward extending outlet ports 109 of the parenteral fluid bags 76, the other end portions of said flexible lines having been heretofore suitably attached to the inlet ports 87 of the drip chamber 86 in the fluid network 84.

As heretofore described, in each drip chamber 86 are two inlet ports; one 87 for a unit of parenteral fluid and the other 88 for a dilutent, if necessary. Immediately below each spike port 108 in the tubing 114 leading to the drip chamber 86 is a roller clamp 116 and in the segment 115 of tubing immediately below the drip chamber 86 is another roller clamp 117.

When packed red cells are used as the parenteral fluid for resuscitation, it is advantageous to increase flow rate by adding normal saline to reduce the viscosity of the packed red cells. Normal saline is added to a packed red cell bag 76 by closing off the roller clamp 117 in the line immediately below the drip chamber 86 serially connected to the parental fluid bag 76 and opening the roller clamp 119 in the line segment 118 connected to the outlet of the saline bag (not shown) via spike 107 containing normal saline and opening clamp 116 in line segment 114 to bag 76 containing the packed red cells. The normal saline bag is then squeezed to cause the saline to flow from the saline bag into the packed red cell bag 76, thereby diluting the packed blood cells. After sufficient saline has been added, the roller clamp 119 in the line 118 leading from the normal saline bag is closed off and diluted blood is now ready to enter the system.

Thereafter, the roller clamp 117 in the line segment 115 below the drip chamber 86 is opened and diluted blood is permitted to flow directly into the system. Thus, it will be appreciated that three roller clamps 116, 117, 119 on each side of a drip chamber 86 are needed for diluting blood with normal saline. Also, that roller clamps 116 are required in the line segments 114 connected to the outlet ports 109 of the IV bags 76 to prevent accidental air embolization. Also, that roller clamps 116 and 119 are required in the line segments 114 and 118 to prevent leakage of fluid out of the system when the lines 114 and/or 118 are not in use.

If only normal saline is administered to a patient, roller clamps 119 in the line segments 118 connected to the saline bags will be open and roller clamps 116 in the unused line segments 114 (which serve no purpose) will be closed off to prevent air from entering the system and fluid leakage from the system.

The four IV line segments 114 leading from the parenteral fluid bags 76 join together in a common flow path at the confluence chamber 89 directly downstream of the drip chambers 86. A ball check valve 120 is provided at each confluence chamber inlet port 90 to prevent accidental retrograde flow into the IV lines 115. Retrograde flow an occur, by way of example, when the roller clamps 117 below the drip chambers 86 are accidently left open during replacement of a parenteral fluid bag 76 or when some bags 76 are empty and fluid is present in the other bags 76 or after a pressure infusor cuff 77 deflates after being disconnected from the pressure source, thereby reducing the pressure of the corresponding parenteral fluid bag 76 as compared to the other bags 76 which are under a pressure of about 300 mm. of mercury.

Although retrograde flow is not entirely eliminated by the ball check valves 120, it is significantly reduced to a fraction of the maximum flow and essentially eliminated from the system. The large confluence chamber 89 serves a dual purpose, namely, to consolidate separate parental fluid flows from the drip chambers 86 into a single flow and to provide a large single drip chamber 89 for measuring the flow rate of the total system by correlating the number of drops per minute through the confluence chamber 89 with the flow rate in cc. per minute.

The confluence chamber 89 includes a transparent cylindrical center member 121 for observing the drip rate of parenteral fluid through the chamber 89, an inlet cap member 122 sealingly attached to one end portion of the center member 121, said inlet member 122 having the four upwardly extending inlet port 90 for attaching the flexible line segments 115 from the drip chambers 86, the check valve 120 in each of said inlet ports 90, a collector cone 123 directly below the ball check valves 120, and an outlet member 124 sealingly attached to the other end portion of the transparent center member 121, said outlet member 124 having the single downward extending outlet port 91 of greater diameter than the inlet ports 90.

One portion of each ball check valve 120 is formed integrally with the inlet port 90 and consists of a conical valve seat 125 and a bore 126 for guiding a ball 127. When retrograde flow is initiated, the ball 127 moves upwardly in the bore 126 and is pressed by the retrograde flow against the conical seat 125 to terminate the reflow. During normal flow conditions, the ball 127 is urged by gravity and parenteral fluid flow to move downwardly away from the conical seat 125 and bear against an orifice plate 128 extending across the confluence chamber 89. Aligned with the ball 127 is an orifice 129 in said plate 128 which is suitably shaped to allow flow to pass around the ball 127. Directly below the orifice plate 128 is the funnel shaped collector member 123 with a downwardly extending tubular port 131 for combining the flow from the separate IV lines 114 into a single flow.

Since the primary use of the present invention is to administer massive infusions, a maximum parenteral fluid flow rate will be maintained until a patient is stabilized. However, once the patient is stabilized, it will be necessary to adjust the flow rate and it is awkward and time consuming to use the four roller clamps 116 below the individual bags 76 to establish flow rate. For this reason a roller clamp 132 is provided in the line segment 133 which is connected to the outlet port 91 of the confluence chamber 89. It is preferable to use the roller clamp 132 directly below the confluence chamber 89 to adjust the drip rate of the confluence chamber 89 for regulating the combined flow rate of the four IV bags 76 simultaneously.

After passing through the confluence chamber 89, the parenteral fluid enters one section of the heat exchanger 93, hereinafter more fully disclosed, wherein the temperature of the parenteral fluid is raised to a normal body temperature of approximately 37 degrees centigrade. The line segment 133 is connected to the heat exchanger 93 by means of conventional tube clamps or other suitable means.

The parenteral fluid then enters the filter 95 for removal of particles and other debris. The filter 95 is conventional for blood delivery equipment except for a larger diameter inlet 96 and outlet 97 ports to accommodate the increased rate of parenteral fluid flow over current systems.

Filters 95 are ineffective after transfusing approximately five units of blood, mainly because accumulations of debris significantly decrease flow, requiring frequent replacement of the filters 95. A pair of the low cost disposable quick connect/disconnect couplings 134 connect the lines to the inlet 96 and outlet 97 ports of the filter 95. The quick connect/disconnect couplings 134 simplify filter 95 replacement, reduce filter 95 replacement time and minimize fluid leakage and the entry of air during filter 95 replacement.

Referring now to FIGS. 22 through 30, inclusive, the particular embodiment of the low cost quick connect-/disconnect coupling 134 disclosed therein for connecting the filter 95 to the fluid flow circuit 84 and to connect the inlet 235 and outlet 236 ports on the water side of the heat exchanger 93.

One feature of the coupling 134 is that the members 135 and 137 of the coupling 134 must be in at least partial locking engagement to establish a fluid path whereby fluid can flow through the coupling 134. Thus, it will be appreciated this feature provides advantages over prior fluid delivery apparatus by reducing the time for replacing the filter and providing assurance there will be no fluid leakage or entry of air during coupling and de-coupling.

Another feature of the disposable coupling 134 is that it consists of very few parts, thus providing low cost and improved reliability. The members 135 and 137 are coupled together by telescopingly engaging their respective outer tubular housings 138 and 139 whereby the outwardly projecting locking pin 140 of one housing 138 engages the J-slot 141 of the other housing 139 and thereafter rotating said housings 138 and 139 so as to fully engage the locking pin 140 with the J-slot 141. An O-ring seal 151 is provided between the housings 138 and 139 to prevent leakage of the parental fluid.

In the interiors of the coupling members 135 and 137 are valve sleeves 142 which are identical and move axially with respect to each other to control the flow of fluid through the coupling 134. The valve sleeve member 142, being generally of tubular shape, has a central aperture 143 which is open at one end 144 to the fluid path. On the end portion of the wall surrounding the central aperture 143 of the valve sleeve 142 are three equally spaced cusps 145.

One portion 146 of each valve sleeve cusp 145 is disposed normal to the axis of the sleeve 142 and serves as a lead during the initial rotational engagement of the locking pin 140 and J-slot 141 during which there is no flow through the coupling members 135 and 137. The remaining portion 147 of each cusp 145 is disposed angularly to the axis of the sleeve 142 and acts as a ramp 147 whereby when the coupling members are rotated to further engage the locking pin 140 and J-slot 141, the ramps 147 of the valve sleeves 142 co-act to move the sleeve 142 axially outward within their respective housings 138 and 139 and open a fluid path through the coupling 134.

On the other end portion 148 of the sleeve 142 opposite the open end cusp portion 144 is an outwardly projecting sealing flange 149 having three equally spaced arcuate tab portions 150 which slideably engage longitudinal grooves 152 in the interior of the outer housings 138 and 139 so as to space the outer edge portion of the sealing flange 149 between said tabs 150 away from the inner surface of said housings 138 and 139 and radially position the valve sleeve 142 within the housings 138 and 139. Adjacent to the sealing flange portion 149 and spaced radially around the tubular portion of the valve sleeve 142 are a pair of fenestrations 153 through which fluid flows outwardly from the interior of the valve sleeve 142 when the valve sleeves 142 are axially disposed.

In the interior of each valve housings 138 and 139 are inwardly projecting annular sealing flanges 154 and sealing rings 155 normal to and concentric with the axes of the housings 138 and 139. When the coupling members 135 and 137 are de-coupled, the housing sealing flanges 154 and sealing rings 155 are pressed against the valve sleeve sealing flanges 149 by coil springs 156 around the valve sleeves 142 and prevent fluid flow through the coupling 134. The coil springs are retained on the valve sleeves 142 by retainers 157 which grip the outer surfaces of the sleeves 142 or other suitable means.

When filters are replaced in current parenteral fluid delivery equipment roller clamps on the inlet and outlet side of the filters must be closed off to prevent fluid leakage. It will be appreciated that with the present invention 40 there is no longer a need to close off clamps on opposite sides of the filter 95 since accidental leakage of blood and introduction of air cannot occur because flow is automatically interrupted when the quick connect/disconnect couplings 134 are de-coupled.

After passing through the filter 95, the fluid enters the combination bubble trap and eliminator 100 wherein air is purged to prevent the exposure of a patient to air embolism. Air can enter the fluid network when the system is opened, such as during replacement of the parenteral fluid bags 76. Additionally, after the bags 76 are emptied of fluid, small amounts of residual air remain in the bags 76. If the fluid is then entirely squeezed out of the bags 76 by the pressure infusers 77, some air can be introduced into the fluid network. Also, when the temperature of the blood is raised from a storage temperature of 4 degrees centigrade to 37 degrees centigrade, approximately 3 cc. of air is liberated per unit of blood.

Since approximately 50 cc. of free air must be rapidly administered to produce an embolism, relatively small quantities of air are not significant and are rapidly dissolved by the patient's own circulating blood. However, during the administration of multiple transfusions to a patient, excessive accumulations of air, from ordinary sources such as replacement of bags 76 or inadvertent actions such as failure of a quick connect/disconnect coupling 134, may result in air embolism without purging by the bubble trap and eliminator 100.

With reference to FIGS. 17 through 21, inclusive, the particular embodiment of a bubble trap and eliminator 100 disclosed therein is generally cylindrical shaped and comprised of an inlet cap 158 having an upwardly extending inlet port 101 for connecting the bubble trap and eliminator 100 to the line segment from the filter 95 and another upwardly extending vent port 159 for purging air from the parenteral fluid, a transparent tubular center member 160 attached to the inlet cap 158 having an apertured guide portion 161 therein for receiving a valve 162, a valve 162 slideably engaging said guide portion 161, a lower valve seat plate 170, and an outlet cap 163 attached to said center member having downwardly extending outlet ports 164 for connecting lines 106 for infusing parenteral fluid into a patient.

The slide valve 162 is aligned with the vent port 159 of the inlet cap 158 and comprises a cylindrical rod 166 having smaller diameter end portions 167, an upper reslient sealing member 168 fixedly attached to one end portion of the rod 166, a lower resilient sealing member 169 fixedly attached to the opposite end portion of the rod 166. The lower sealing member 169 has a hollow spherical float portion 171, adjoining a cylindrical portion 172 having a conical sealing portion 173 at the end thereof. The upper sealing member 168, being generally cylindrical in shape, has a conical sealing element 175 at the upper end portion thereof. The sealing members 168 and 169 are retained to the valve rod 166 by engaging arcuate rib portions 176 of the slider rod with internal arcuate recesses 177 of the sealing members 168 and 169.

When a substantial amount of air is accumulated in the bubble trap and eliminator 100, the fluid level is low and the weight of the slide valve 162 causes the valve 162 to fall and the conical end portion 173 of the lower sealing member 169 to press against the conical seat 178 of the lower valve seat plate 170. Thus, the outlet ports 164 are sealed off and the interior of the bubble trap and eliminator 100 is vented to the atmosphere through a fibrous filter 165 whereby air is discharged through the vent port 159 without fluid flow through the trap and eliminator 100.

As the bubble trap and eliminator 100 fills with parenteral fluid, the buoyant force of the fluid acts on float 171 and causes the valve 162 to rise whereby the upper sealing member 168 presses against the conical seat 179 of the vent port 159 and the lower sealing member 169 is unseated from the lower seat 178. This allows fluid to flow through the trap and eliminator 100 without permitting fluid leakage through the vent port 159.

Since the bubble trap and eliminator 100 is effective only in an upright or near upright position, when the fluid network 84 is disconnected from the apparatus 40 during the transport of a patient and the bubble trap and eliminator 100 is placed next to the patient in a horizontal position, the vent port 159 must be sealed off to prevent fluid loss and massive air embolization. For this condition a pinch clamp 180 is provided in a vent line attached to the vent port 159 which seals off the vent port 159.

After flowing through the bubble trap and eliminator 100 the parenteral fluid flows through five IV lines 106, sufficiently long to enable infusion of the parental fluid at the most distant parts of the patient. Within about six inches of each catheter at the distal end of a line 106 is the IV injection port 105 and a roller clamp 183 proximal to and ahead of the IV injection port 182. The purpose of the roller clamp 183 is threefold: (1) to close off an IV tube 106 when it is not in use, (2) to close off the flow of parenteral fluid during a separate infusion by gravity flow of medication through the IV port 105, and (3) to permit taking of central venous pressure (CVP) measurements.

It will be appreciated because the parenteral fluid is under pressure that if a line from the bubble trap and eliminator 100 is left open when medication is introduced through an injection port 105 in the line 106 retrograde flow of the parenteral fluid will occur through the line 106 and into the bottle of the medication unless the roller clamp 183 ahead of the IV injection port 105 is closed off whereby medication then can be administered without retrograde flow through the IV port 105 directly into the patient. With this arrangement infection and disruption of the system are prevented because it is not necessary to disconnect the tubing 106 in order to administer medication.

For improved organization, unused IV lines 106 are preferably coiled up and loosely tied at the bubble trap and eliminator 100 whereby their distal ends are exposed to view so that the lines 106 may be readily located when the need to use the lines 106 arises.

PRESSURE DELIVERY CIRCUIT

With reference to FIGS. 10 and 12, the particular embodiment of the pressure delivery circuit 85 disclosed therein comprises a pressure cylinder 71 in the interior of the portable cabinet 41 filled with compressed nitrogen, air or another suitable gas; a manual on/off valve 185 mounted to the top of the cylinder 71; an auxiliary port 190 mounted to the side of the cabinet 41 and operably connected in parallel with the pressure tank outlet 186 for receiving an alternate supply of compressed gas; an operator actuated control 187 serially connected to the cylinder 71, a regulator 188 serially connected to the operator control 187 for reducing the pressure of the stored gas to about 300 mm. of mercury; an expansible infuser 77 at each parenteral fluid bag 76 serially connected to the pressure regulator 188 for increasing the rate of flow of parenteral fluid out of said bags 76, and tubular line means for interconnecting the members of the pressure delivery system 85.

The manual on/off valve 185 on top of the pressure cylinder 71 is of conventional construction and is used during replacement of the pressure cylinder 71 as well as during service of the pressure delivery system 85 and connecting an alternate source of compressed gas such as a centralized hospital nitrogen system (not shown). The valve 185 is configured whereby the auxiliary port 190 is open only when the flow of gas from the cylinder 71 is closed off (by the manual valve 185) so that only one pressure source can be used at any given time.

The auxiliary gas port 190 is suitably attached to the right wall 49 of the cabinet 41 and preferably comprises one member 203 of a conventional spring loaded double valve quick connect/disconnect coupling 204 whereby an auxiliary gas supply can be conveniently connected to the apparatus 40. A line 191 connected to the rear portion of the manual on/off valve 185 operatively connects the auxiliary port 190 to the pressure delivery system 85.

The operator control 187, hereinafter more fully described, is mounted in the recess 54 of the cabinet countertop 46 and is a conventional pneumatic rotary valve with a test override off position. In the test override position, the flow of gas from the cylinder 71 or an alternate auxiliary pressure source is closed off and the line segment 192 ahead of the control 187 vented whereby the line pressure is reduced to atmospheric pressure. The outlet port 266 of the control 187 is serially connected by a line segment 192 to a housing 193 whereat a transducer 194 monitors the supply pressure in the cylinder 71 or an alternate auxiliary pressure source.

The pressure transducer housing 193 is serially connected by a line segment 195 to the pressure regulator 188 which is located inside the cabinet vertical support member 72 wherein the supply pressure is reduced to the infuser pressure of about 300 mm's of Hg. The outlet port 199 of the regulator 188 is serially connected by a line segment 200 to the inlet pot 197 of a 4×1 coupling 198 inside the vertical cabinet member 72 whereby the flow of gas divides into four parallel paths. The four coupling outlet ports 201 are connected by line segments 202 to members 78 of conventional type spring biased single valve quick connect/disconnect couplings 68 suitably attached to the lower crossmember 74 of the portable cabinet 41 whereby when the couplings 68 are de-coupled, the lines 202 which extend to the 1×4 coupling 198 are sealed against leakage of gas.

The members 78 of the couplings 68 extend through apertures 205 of the crossmember 74 whereby the coupling members 78 are externally accessible for coupling the corresponding coupling members 267 of lines 79 which supply the 300 mm's pressure to the parenteral bag infuser cuffs 77. With reference to FIGS. 1 and 2, the pressure infuser cuffs 77 are conventional units which are commonly applied with a hand pump for infusion of parenteral fluids or any other suitable means for squeezing the flexible parenteral fluid bags 76 to increase the rate of fluid flow. The infuser cuffs 77 surround the fluid bags and are mounted on the upper crossmember 73 via hooks 75 and oriented with respect to the parenteral fluid bags 76 such that the semi-transparent portions 207 of the infuser cuffs 77 which allow the operator to observe the fluid levels in the bags 76 face the operator's side of the cabinet 41.

In each line running from a pressure infuser cuff 77 to the quick connect/disconnect coupling 68 is a conventional clamp 208 to seal off the line 79 when the parenteral fluid bag 76 and its respective pressure infuser cuff 77 are removed from the apparatus 40 during the transport of a patient whereby the fluid bag 76 may remain pressurized during the transport of the patient. In addition to the four pressure infuser cuffs 77, mounted on the fluid warming and delivery apparatus 40, several spare infuser cuffs 77 (not shown) are preferably available to permit pre-loading into the spare infuser cuffs 77 with full parenteral fluid bags 76 prior to installation in the apparatus 40.

THE PARENTERAL FLUID WARMING SYSTEM

With reference to FIGS. 10 and 12, the particular embodiment of the parenteral fluid warming system 43 disclosed therein is a closed recirculating system comprising a water reservoir tank 209 mounted inside the portable cabinet 41, a heating means for maintaining the temperature of the water at about 37 degrees centigrade, a pump 211 for recirculating the water through the warming system 43, the heat exchanger 93 for transferring heat from the recirculating water to the parenteral fluid of the fluid supply system 42 and lines 212 for interconnecting the members of the warming system 43.

The water reservoir tank 209, being of generally rectangular shape, has a total volume of about 6 gallons, 5 gallons of which is usable for storing water and the remaining one gallon of which provides an air space above the water. The tank 209 is fixedly mounted to the interior of the portable cabinet 41 by some suitable means and the entire exterior of the tank 209 is preferably covered with a layer of insulation 213 about one inch thick.

A water filler tube 196 extends through an aperture 216 in the top wall 217 of the tank 209 and is fixedly mounted to said wall 217. At the upper end of the tube 196 is a removable closure 218 for adding water to the tank 209. The closure 218 is accessible through the cabinet storage compartment door 66 on the operator's side. The lower end portion of the filler tube 196 extends partially into the tank 209 to a depth whereby during filling the flow is cut off at about 5 gallons when the lower end portion of the tube 196 is covered by water and the remaining air above the water is prevented from exiting the tank 209. The closure 218 is a conventional unit with pressure relief and vent valves to compensate for volumetric changes in heating water caused by temperature changes.

Directly below the lower end portion of a water return line 214 in the interior of the reservoir tank is an umbrella shaped diffuser 215 which distributes and mixes incoming water with the higher temperature water within the tank 209. The umbrella shaped diffuser 215 has outward extending portions 219 fixedly attached to the side walls 220 of the tank 209 by some suitable means.

Fixedly attached to one side wall 220 of the reservoir tank 209 and projecting into the interior of the reservoir tank 209 is a conventional primary electric heating element 210. When water is not circulated through the system 43 and particularly while the apparatus 40 is maintained in a "stand by" condition the primary electric heating element 210 is energized to maintain the water in the reservoir tank 209 at about 37 degrees centigrade whereby the apparatus 40 can immediately become operative for transfusing warmed parenteral fluid into a patient. Also mounted to the reservoir tank 209 is a temperature transducer 224 hereinafter more fully described.

At the lower portion of the tank 209 is an outlet line 222 which connects the reservoir tank 209 to the pump 211 adjacent to the reservoir tank 209 and fixedly mounted to the cabinet lower wall 45. Included in the line 222 between the tank 209 and the pump 211 is a conventional type of drain 271 for emptying the tank 209 of water. The pump 211 is driven by an electric motor 223 and circulates the water through the parenteral fluid warming system 43. The outlet port 227 of the pump 211 is connected to a housing 225 whereat a second temperature transducer 226 hereinafter more fully described is mounted. At the outlet port 240 of the transducer housing 225 is connected a larger diameter line segment 228 which extends to another housing 229 whereat a third temperature transducer 230 hereinafter more fully described is mounted.

Inside the larger diameter line segment 228 is a secondary heating element 231 which maintains the temperature of the circulating water within a narrow temperature band. The secondary heating element 231 is energized when the pump 211 is operative and is de-energized when the pump 211 is inoperative.

The pump 211 is preferably sized to provide a flow rate of approximately 10 liters or 2½ gallons a minute for the apparatus herein disclosed. Since the reservoir tank 209 holds about 5 gallons of water, the water will be entirely circulated through the system in approximately two minutes. It will be appreciated that the optimum flow rate for the circulating water is dependent on the particular heat exchanger and may vary from a rate of 2½ gallons per minute. It is to be noted that by operating the secondary heating element only during the time the primary heating element is inoperative and vice versa, the electrical load on the hospital electrical system can be more easily maintained within the maximum limit without loss in performance of the fluid warming system 43.

The outlet port 232 of the second transducer housing 229 is connected to a flow rate meter 268 wherefrom a reduced diameter line segment 233 extends through an aperture 234 in the top wall 46 of the cabinet 41 and is connected to an inlet port 235 of the heat exchanger 93 by the low cost disposable quick connect/disconnect coupling 134 hereinbefore described.

The heat exchanger 93 is a high efficiency folded plate counterflow unit suitably mounted to the cabinet vertical support member 72 wherein the parenteral fluid enters the inlet port 94 on one side of the heat exchanger 93 and flows upwardly to an outlet port 99 of said heat exchanger 93 and the warming water enters the inlet port 235 on the upper portion of the other side of the heat exchanger 93 and flows downwardly to an outlet port 236 on the lower portion of the heat exchanger 93.

After exiting the heat exchanger 93 through a low cost disposable quick connect/disconnect coupling 134 hereinbefore described, the water flows through the return line which is routed through an aperture 234 in the top wall 46 of the portable cabinet 41, into the reservoir tank 209, directly above the center portion of the umbrella shaped diffuser 215.

GAUGES AND CONTROLS

Control Panel

The operator gauges 59 and controls 58 comprise an on/off/standby control 238 for activating the electrical systems of the apparatus 40, a control 187 for admitting pressurized gas to the parenteral fluid infuser cuffs 77, gauges 59 for monitoring the performance of the apparatus systems, a buzzer (not shown) mounted inside the control box 239 for alerting an operator when a system malfunction occurs and means for checking each of the failure warning systems. It will be later observed that a feature of the invention is that each of the failure warning systems is checked by simulating failure to activate the warning systems.

As hereinbefore described, the electrical on/off/standby control 238, pressure infuser operator control 187 and warning system test controls 269 and 270 are mounted below the L-cover 55 of the portable cabinet 41 to prevent damage or accidental actuations thereof at inappropriate times.

With reference to FIG. 6, the control panel 241 on the countertop 46 includes a pressure gauge 242, a temperature gauge 243, a low pressure light 244, a high temperature light 245, a low temperature light 246, a low flow light 247, a low reservoir light 248 and a reset control 249. To quickly identify the source of a problem when the warning buzzer (not shown) sounds, indicator lights and gauges 242 through 248 of the various systems are preferably differentiated by different colors and clustered together in the control panel 241 on the cabinet countertop 46. After the reset control 249 is pressed, the buzzer (not shown) is silenced until another problem occurs, however, the particular warning lights 244 through 248 will remain lit until the problem is corrected.

To insure all warning systems are operative, all indicator lights 244 through 248 and the warning buzzer (not shown) are momentarily activated when the apparatus 40 is turned on and off. Should a problem exist when the unit 40 is turned on or off, the buzzer (not shown) will continue to sound until the reset control 249 is pressed and the indicator lights 244 through 248 of the malfunctioning system will remain lit until the problem is corrected.

Reservoir Tank Water Level

With reference to FIGS. 31 through 33, the water level in the reservoir tank 209 is monitored by a graduated sight glass 250 which is visible through an aperture 251 in the cabinet rear wall 48 on the operator's side of the portable cabinet 41. The upper end portion of the sight glass 250 is open whereas the lower end portion of the sight glass 250 is sealingly mounted to the upper end portion of a housing 252. The housing 252 has a vertical passage 253 which is aligned with the sight glass 250 and selectively communicates with the interior of the water reservoir tank 209 by a manually operated rotary valve 254. The housing 252 is secured with threaded fasteners 255 to a mounting plate 256 affixed to the reservoir tank 209. Between the housing 252 and the reservoir tank 209 is a gasket 257 which provides a water tight seal at the interface of the housing 252 and tank 209.

Referring now to FIG. 33, a horizontal passage 258 extends through the housing 252 and rotatably receives the cylindrical valve 254. The valve 254 has one transverse aperture 259 and another transverse aperture 260 which is normal to and communicates with the first transverse aperture 259. The outer end portion 261 of the valve 254 receives a control knob 262 for manually rotating the valve 254.

When the valve 254 is rotated by the operator whereby the first transverse aperture 259 of the valve 254 is horizontally disposed a flow path is established from the reservoir tank 209 to the sight glass 250 whereby the sight glass 250 is filled to the same water level of the tank 209. Alternatively, when the valve 254 is rotated clockwise by the operator to a position 90 degrees from the aforementioned position, the second transverse aperture 260 is horizontally disposed and a flow path is established from the interior of the sight glass 250 to a downward extending tube 265 wherein the water in the sight glass 250 is substantially drained.

In the housing vertical passage 253 which is aligned with the sight glass 250 is a vertically disposed proximity switch 263, commonly referred to as a reed switch. Slideably mounted on the exterior of the proximity switch 263 is a magnetic float 264 which rises as the vertical passage 253 is filled with water, causing the contacts of the proximity switch 263 to open. In the event the water level in the tank 209 falls below a predetermined unacceptable level, the corresponding drop of water level in the sight glass 250 and housing 252 causes a downward movement of the magnetic float 264 whereby the contacts of the proximity switch 263 close and activate the warning buzzer (not shown) and low water indicator light 248.

It will be observed with the foregoing arrangement that a failure mode for insufficient water in the reservoir tank 209 can be easily simulated to test the warning system by rotating the valve 254 such that the second transverse aperture 260 of the valve 254 is horizontally disposed to shut off flow from the reservoir tank 209 and empty the water in the housing 252 through the downward extending tube 265 attached to the housing 252.

Pressure Delivery Circuit

The performance of the pressure delivery circuit 85 is monitored by the pressure transducer 194, positioned between operator control 187 and regulator 188, which supplies a voltage to a suitable electrical control circuit (not shown) for operating the pressure gauge 242 on the cabinet countertop 46. In the event gas in the cylinder 71 is depleted such that the pressure falls to an unacceptable level, the buzzer (not shown) and indicator light 244 will be activated by the pressure transducer 194. During a test of the failure warning system, the operator control 187 is rotated to the test position whereby the pressure from the pressure source is cut off and line 192 to the regulator 188 vented so that the pressure sensed by the transducer 194 is zero and the buzzer warning system activated.

Fluid Warming System

With reference to FIG. 7, a temperature sensing transducer 224 provided in the water reservoir tank 209 supplies a voltage to a suitable control circuit (not shown) for energizing the reservoir heating coil 210 when the temperature in the reservoir tank 209 is less than 37 degrees centigrade and the water pump 211 is inoperative. The water pump 211 is inoperative when the apparatus 40 is in a stand-by condition or when a failure condition causes the pump 211 and heater 231 to be shut off. Should the reservoir tank 209 water temperature fall below a value deemed unacceptable in accordance with the normal performance of the fluid warming system 43 the transducer 224 in the reservoir tank 209 will activate the buzzer (not shown) and warning light 246 to alert the operator to the problem.

While water is being circulated through the warming system 43 by the pump 211, the second temperature sensing transducer 226 at the inlet side of the secondary heating coil 231 supplies a voltage to a suitable control circuit (not shown) for energizing the secondary heating coil 231 to maintain the temperature of the water at the inlet port 235 of the heat exchanger 93 at 37 degrees centigrade. The third temperature transducer 230 on the outlet side of the secondary heating coil 231 is a high limit transducer 230 which interrupts the current to the secondary heating coil 231 and pump 211 and activates the alarm buzzer (not shown) and warning light 245 in the event the water temperature should exceed a high limit of about 40 degrees centigrade.

Also on the outlet side of the secondary heating coil 231 is the flow rate meter 268 for supplying voltage to a suitable control circuit (not shown) which activates the warning buzzer (not shown) and warning light 247 and shuts down the pump 211 and heating coil 231 in the event the flow rate falls below a level which is inadequate for warming the parenteral fluid.

The testing of the water warming and pump circuits is accomplished by simulating failure. An excessive temperature failure is simulated by electrically disabling the temperature transducer 226 and sending a falsely lowered temperature signal instead. This will, in turn, cause the secondary heating coil 231 to overheat the warming water, which will trigger the temperature overheat warning light 245 and the buzzer (not shown).

A low flow failure is simulated by reducing motor 223 and pump 211 output by one-half, thereby triggering the buzzer (not shown) and the low flow warning light 247.

Thus, multiple ways of assuring system performance are provided to provide a fail safe system and a higher reliability than heretofore available in parenteral fluid warming and delivery equipment.

Although but a single embodiment of the present invention has been disclosed and described in detail herein, it will be appreciated that other embodiments incorporating the features of the invention can be provided without departing from the spirit thereof.

I claim:

1. Apparatus for the rapid warming and infusion of massive amounts of a parenteral fluid into a patient under conditions where time is of the essence comprising in combination:

(a) a pressurized parenteral fluid supply means for rapidly infusing massive amounts of parenteral fluid into a patient, including a disposable fluid flow circuit means connected to the fluid supply bags for supplying and infusing the parenteral fluid into the patient, and a pressure delivery circuit means operably connected to said fluid flow circuit for rapidly infusing massive amounts of the parenteral fluid into the patient;

(b) a fluid warming system operably connected to the pressurized parenteral fluid supply system and having means for warming massive amounts of parenteral fluid prior to infusion of said fluid into the patient;

(c) means for controlling the temperature of the parenteral fluid;

(d) means for controlling the rate of discharge of the parenteral fluid, said disposable fluid flow circuit having a liquid heat exchanger with said disposable fluid flow circuit means having;

(1) at least one parenteral fluid bag for providing the parenteral fluid, said bag having an outlet port for discharging the parenteral fluid from the bag;

(2) a drip chamber for monitoring the rate of fluid discharge from the parenteral fluid bag, said drip chamber having an inlet port serially connected to the outlet port of the parenteral fluid bag and an outlet port;

(3) a portion of said heat exchanger through which the parenteral fluid flows, said heat exchanger having an inlet port serially connected to the drip chamber outlet port and an outlet port;

(4) flexible tubular means for interconnecting members of the fluid flow circuit means, said tubular means having at least one distal end portion adapted for attaching a catheter to infuse the parenteral fluid into the patient; and (5) means for controlling the discharge of the parenteral fluid from the distal end of said tubular means.

2. The apparatus recited in claim 1 wherein said disposable fluid flow circuit has a liquid heat exchanger and said disposable fluid flow circuit means comprises:

(a) a plurality of parenteral fluid bags for providing the parenteral fluid, each of said bags having an outlet port for discharging the parenteral fluid from the bags;

(b) a plurality of drip chambers for monitoring the rate of fluid discharge from each of the parenteral fluid bags, each of said drip chambers having an inlet port connected to the outlet port of a corresponding fluid bag and an outlet port for discharging the parenteral fluid;

(c) a confluence chamber for combining the discharge of parenteral fluid from the outlet ports of the drip chambers, said confluence chamber having a plurality of inlet ports and an outlet port, each inlet port thereof being connected to an outlet port of a corresponding drip chamber;

(d) a portion of said heat exchanger through which the parenteral fluid flows, said heat exchanger having an inlet port serially connected to the confluence chamber outlet port and an outlet port;

(e) flexible tubular means for interconnecting members of the fluid flow circuit means, said tubular means having distal end portions adapted for attaching catheters to infuse parenteral fluid into the patient at multiple locations; and (f) means for controlling the discharge of parenteral fluid from the distal ends of said tubular means.

3. The apparatus recited in claim 2 wherein means are provided in said confluence chamber to prevent reversal of the flow of parenteral fluid in said chamber.

4. The apparatus recited in claim 2 wherein said confluence chamber further comprises:

(a) an inlet cap, the upper portion thereof forming the plurality of upward extending inlet ports for receiving parenteral fluid from said drip chambers, each of said ports having said means for preventing reverse flow of parenteral fluid in the confluence chamber;

(b) a downward tapering collector member below the inlet cap for uniting the parenteral fluid flowing through said inlet ports into a unitary flow, said collector member having a downward extending outlet port at the lower end portion thereof for discharging a single stream of parenteral fluid from said member;

(c) a center transparent housing enclosing said collector member and sealingly attached to said inlet cap; and (d) an outlet cap having an outlet port forming the lower portion thereof, sealingly attached to said center housing, for discharging parenteral fluid from the confluence chamber.

5. The apparatus recited in claim 1 wherein said drip chamber has a second inlet port for injecting a dilutent to reduce the viscosity of the parenteral fluid.

6. The apparatus recited in claim 1 further comprising a filter having an inlet port for receiving the parenteral fluid and an outlet port for discharging said fluid, said inlet port being serially connected to the outlet of said heat exchanger portion.

7. The apparatus recited in claim 6 further comprising a bubble trap and eliminator for purging air from the parenteral fluid to prevent an air embolism in the patient, said bubble trap and eliminator having an inlet port serially connected to the outlet port of said filter for receiving the parenteral fluid and a plurality of outlet ports for discharging said fluid into multiple line segments to provide a plurality of distal ends.

8. The apparatus recited in claim 7 wherein said bubble trap and eliminator comprises:

(a) an inlet cap having an upwardly extending inlet port on the upper portion thereof for admitting parenteral fluid into the bubble trap and eliminator and an upwardly extending vent port for purging air from the bubble trap and eliminator;

(b) a center housing sealingly attached at the upper end thereof to the inlet cap, said housing having means in the interior thereof for locating and guiding a valve;

(c) a plate subtending the lower portion of the center housing, said plate having a downwardly extending outlet port aligned with the vent port of the inlet cap;

(d) a valve mounted for reciprocal vertical movement in said center housing, said valve having a slender cylindrical center portion, a resilient upper sealing portion, a resilient lower sealing portion and a float portion therebetween for sealing the vent port when the bubble trap and eliminator is substantially filled with parenteral fluid and sealing the outlet port of said plate when the bubble trap and eliminator is substantially empty of parenteral fluid; and (e) an outlet cap sealingly attached to said central housing and having an outlet port for the discharge of parenteral fluid from the bubble trap and eliminator.

9. The apparatus recited in claim 1 wherein said means for controlling the rate of discharge of parenteral fluid from the distal end portion of the flexible tubular means is a manually adjustable clamp attached to said flexible tubular means.

10. The apparatus recited in claim 1 wherein said heat exchanger is a counterflow heat exchanger.

11. Apparatus for the rapid warming and infusion of massive amounts of a parenteral fluid into a patient under conditions where time is of the essence comprising in combination:
   (a) a pressurized parenteral fluid supply system having means for rapidly infusing massive amounts of parenteral fluid into a patient, including a disposable fluid flow circuit means connected to the fluid supply bags for supplying and infusing the parenteral fluid into the patient, and a pressure delivery circuit means operably connected to said fluid flow circuit for rapidly infusing massive amounts of the parenteral fluid into the patient, said pressure delivery circuit having
      (1) a cylinder for storing gas under pressure;
      (2) a manual on/off valve for controlling the discharge of gas from the cylinder;
      (3) a regulator valve serially connected to said manual on/off valve for reducing the pressure of the gas supplied by said cylinder to a predetermined lower pressure;
      (4) an operator valve serially connected to the regulator valve for controlling the flow of said gas by an operator;
      (5) a plurality of flexible expansible pressure cuffs serially connected to said operator valve, each of said pressure cuffs enclosing one of said flexible fluid bags for squeezing said bags to rapidly infuse the parenteral fluid into the patient; and
      (6) tubular line means for interconnecting the members of the pressure delivery circuit;
   (b) a fluid warming system operably connected to the pressurized parenteral fluid supply system and having means for warming massive amounts of parenteral fluid prior to infusion of said fluid into the patient;
   (c) means for controlling the temperature of the parenteral fluid; and
   (d) means for controlling the rate of discharge of the parenteral fluid.

12. The apparatus recited in claim 11 further comprising an auxiliary port mounted for admitting a supply of pressurized gas from a source other than the cylinder in said tank and a tubular line means for connecting the auxiliary port to the pressure delivery circuit.

13. The apparatus recited in claim 11 further comprising:
   (a) means in said operator valve for simultaneously closing off the supply of gas on the inlet side of the valve and venting the gas on the outlet side of the valve;
   (b) an indicator light operably connected to the pressure transducer, said light being illuminated when the pressure at the outlet side of the operator valve is below a predetermined value and not being illuminated when the pressure on the outlet side is above said value;
   (c) an audible buzzer and indicator light operably connected to said pressure transducer, said buzzer being actuated and indicator light illuminated when the pressure at the outlet side of the operator valve falls below said predetermined value and not being actuated when the pressure on the outlet side is above said value; and
   (d) a reset means for manually de-activating said buzzer.

14. The apparatus recited in claim 11 further comprising:
   (a) a second pressure sensing transducer positioned between the regulator valve and operator valve; and
   (b) a pressure calibrated gauge operably connected to said pressure transducer for monitoring the condition of the pressure delivery circuit.

15. Apparatus for the rapid warming and infusion of massive amounts of a parenteral fluid into a patient under conditions where time is of the essence comprising in combination:
   (a) a pressurized parenteral fluid supply system having means for rapidly infusing massive amounts of parenteral fluid into a patient;
   (b) a fluid warming system connected to the pressurized parenteral fluid supply system and having means for warming massive amounts of parenteral fluid prior to infusion of said fluid into the patient; said fluid warming system has a liquid heat exchanger and includes
      (1) a reservoir tank for storing a liquid for warming the parenteral fluid;
      (2) a liquid for warming the parenteral fluid;
      (3) a pump operably connected to said tank for re-circulating said liquid through the warming system;
      (4) a portion of said heat exchanger through which said warming system liquid flows, said heat exchanger portion being operably connected to said reservoir tank;
      (5) a primary heating element mounted inside of said reservoir tank for heating said liquid, said primary element being operative only when said pump is inoperative to maintain the apparatus in a stand-by condition;
      (6) a secondary heating element for heating said liquid, said secondary heating element being operative only when said pump is operative and said primary heating element is inoperative to maintain the temperature of the liquid at a predetermined level; and
      (7) tubular line means for operably connecting the members of the fluid warming system,
   (c) means for controlling the temperature of the parenteral fluid;
   (d) means for controlling the rate of discharge of the parenteral fluid.

16. The apparatus recited in claim 15 wherein said means for controlling the temperature of the parenteral fluid comprises:
   (a) a first temperature sensing transducer mounted in said reservoir tank and operably connected to said primary heating element whereby said primary heating element is operative when said pump is inoperative and the temperature in said reservoir tank is below a predetermined value;
   (b) a second temperature sensing transducer mounted on the inlet side of the secondary heating element and operably connected to said secondary heating element whereby said secondary heating element is operative when said pump is operative and the temperature of the liquid on the inlet side of the secondary heating element is below a predetermined value;
(c) a third temperature sensing transducer mounted on the outlet side of the secondary heating element;
(d) means operably connected to said third temperature sensing transducer for making said pump and said primary and secondary heating elements inoperative when the temperature of the liquid on the outlet side of the secondary heating element rises above a predetermined value;
(e) a temperature calibrated gauge operably connected to said third temperature sensing transducer for monitoring the temperature of the liquid on the outlet side of said secondary heating element;
(f) a flow rate meter mounted on the inlet side of the heat exchanger for sensing the flow rate of the liquid in the parenteral fluid warming system;
(g) an indicator light mounted on the cabinet and operably connected to said flow rate meter for monitoring the flow rate of the liquid in the parenteral fluid warming system; and
(h) means for monitoring the level of liquid inside of the reservoir tank.

17. The apparatus recited in claim 16 wherein said means for monitoring the level of liquid inside of the reservoir tank comprises:
(a) a housing mounted to the reservoir tank, said housing having a horizontal passage which communicates with the interior of said tank and an upward extending passage which communicates with said horizontal passage; and
(b) a graduated sight glass having an open upper end portion and a lower end portion sealingly mounted to the housing at the upper end portion of the upwardly extending passage.

18. The apparatus recited in claim 17 wherein said means for monitoring the level of liquid inside the reservoir tank further comprises:
(a) said housing having a downward extending passage for draining liquid from said housing and a transverse bore for receiving a rotary valve, each of the passages communicating with said horizontal passage of said housing;
(b) a manually operable rotary valve, said valve having a first transverse aperture whereat in one position of the valve the flow path between the reservoir tank and sight glass is closed off and a flow path is established between the downward extending passage and the upward extending passage to substantially drain the liquid of the sight glass and upward extending passage so as to simulate a low liquid condition in said reservoir tank;
(c) a vertically disposed proximity switch mounted to said housing within the upward extending passage of said housing;
(d) a magnetic float slideably engaging said proximity switch, said float being positioned on said switch to close the contacts of said switch when the housing is substantially drained of liquid and to open said contact when the housing is substantially filled with liquid;
(e) an indicator light operably connected to the proximity switch, said light being illuminated when the contacts of said switch are closed and not being illuminated when the contacts of said switch are open;
(f) an audible buzzer operably connected to the proximity switch, said buzzer being operative when the contacts of said switch are closed and being inoperative when the contacts of said switch are open; and
(g) a reset means for manually de-activating said buzzer.

19. The apparatus recited in claim 15 wherein the liquid of said fluid warming system is water.

20. Portable apparatus for the rapid warming and infusion of massive amounts of a parenteral fluid into a patient under conditions where time is of the essence comprising in combination:
(a) a portable wheeled cabinet adapted for mounting a pressurized parenteral fluid supply system and a fluid warming system, said cabinet having means for pushing steering said portable apparatus to a patient;
(b) a pressurized parenteral fluid supply system mounted on said cabinet, said pressurized fluid supply system having means for rapidly infusing massive amounts of parenteral fluid into a patient;
(c) a fluid warming system mounted on the cabinet, said warming system operably connected to the pressurized parenteral fluid supply system and having means for warming massive amounts of parenteral fluid prior to infusion of said fluid into the patient;
(d) means for controlling the temperature of the parenteral fluid; and
(e) means for controlling the rate of discharge of the parenteral fluid, said portable cabinet including:
(1) a generally rectangular enclosure carried on swivel casters mounted at the corners thereof, said enclosure having a recessed rear upper portion for mounting apparatus operating and test controls, an upper wall for mounting means for monitoring said fluid supply and warming systems and storing medications and supplies thereon, and door means for access to the interior thereof;
(2) an L-shaped transparent cover pivotally mounted to said upper wall for enclosing said recessed upper cabinet portion;
(3) a generally rectangular vertical support member extending upwardly from the forward portion of said upper wall;
(4) an upper crossmember fixedly attached at the center thereof to the upper portion of said vertical member, said upper crossmember having a plurality of rearward extending hook members for supporting pressure cuffs and parenteral fluid bags; and
(5) a lower crossmember fixedly attached at the center thereof to said vertical member at a location below said upper crossmember for attaching lines to pressurize said parenteral fluid bags.

21. In an apparatus for rapidly warming and infusing a parenteral fluid into a patient under conditions where time is of the essence and of the class where a bubble trap and eliminator having a slideable valve is provided for purging air from the apparatus, the improvement which comprises a resilient conical sealing means at each end portion of said slideable valve for sealing the bubble trap and eliminator against the entry of fluid during the purging of air and alternately sealing the bubble trap and eliminator against the entry of air during the flow of parenteral fluid.

22. In an apparatus for rapidly warming and infusing a parenteral fluid into a patient under conditions where time is of the essence and of the class where replaceable disposable members are provided, the improvement which comprises quick connect/disconnect couplings for the rapid replacement of disposable members having means for preventing spillage of parenteral fluid during the replacement of the disposable members, each of said couplings comprising:

(a) a first cylindrical housing having an aperture in the center thereof for receiving a slideable valve sleeve, said housing having an annular sealing flange projecting inwardly in the center portion of the interior thereof;

(b) a second cylindrical housing slideably engaging said first housing having an aperture in the center thereof for receiving a second slideable valve sleeve, said housing also having an annular sealing flange projecting inwardly in the center portion of the interior thereof;

(c) resilient means for providing a leakproof seal between said first and second housings;

(d) a pair of aligned opposite facing valve sleeves, each sleeve having an open end apertured portion and an opposite end closed cover portion, the open end portions of the sleeves having a plurality of circumferential cusps, each cusp having a lead portion normal to the axis of the respective sleeve and a ramp portion disposed angularly to the axis of the respective sleeve, the outer portion of each cover portion extending outwardly beyond the body of the sleeve and forming a sealing flange, and a plurality of fenestrations extending through the body of each sleeve, adjacent to the cover portion, one sleeve slideably engaging the first housing and the other sleeve slideably engaging the second housing, the cusp portions of each sleeve engaging each other whereby when said first housing is rotated in said second housing the valve sleeves initially maintain the same axial position with respect to each other and thereafter move axially away from each other and separate the sealing flanges of the sleeves from the sealing flanges of the housing to allow fluid to flow through said fenestrations and through said coupling;

(e) a spring means mounted on the body of each valve sleeve for urging the sealing flange of a valve sleeve against the annular sealing flange in the respective housing;

(f) a means for retaining the spring means on the valve sleeves;

(g) resilient means for providing a leakproof seal between the sealing flange of each valve sleeve and the sealing flange of the respective housing; and (h) locking means for fixing the first sleeve to the second sleeve.

23. Apparatus for the rapid warming and infusion of massive amounts of a parenteral fluid into a patient under conditions where time is of the essence comprising in combination:

(a) pressurized parenteral fluid supply means for rapidly infusing a massive amount of parenteral fluid into a patient;

(b) means for warming the massive amount of parenteral fluid prior to the infusion of said fluid into the patient, said means for warming including a heat exchanger means operable for transferring heat to parenteral fluid by the circulation of thermal liquid therethrough and a reservoir containing a thermal liquid for circulation through said heat exchanger (c) means responsive to the temperature of said liquid for controlling the temperature of the parenteral fluid; and (d) means for controlling the rate of discharge of the parenteral fluid.

24. The apparatus recited in claim 23 further comprising a cabinet and means on said cabinet for pushing and steering the apparatus to the patient.

25. The apparatus recited in claim 23 wherein said parenteral fluid supply means is a disposable means.

26. The apparatus recited in claim 23 further comprising quick connect/disconnect means for connecting the members of the fluid supply means.

27. Apparatus for the rapid warming and infusion of massive amounts of a parenteral fluid into a patient under conditions where time is of the essence comprising in combination:

(a) pressurized parenteral fluid supply means for rapidly infusing a massive amount of said parenteral fluid into a patient;

(b) means for warming the massive amount of parenteral fluid prior to the infusion of said fluid into the patient;

(c) means for controlling the temperature of the parenteral fluid;

(d) means for controlling the rate of discharge of the parenteral fluid; and (e) means for maintaining said parenteral fluid warming means in a stand-by condition such that the parenteral fluid is immediately warmed when said apparatus is initially applied for infusing the parenteral fluid into a patient.

28. Apparatus for the rapid warming and infusion of massive amounts of a parenteral fluid into a patient under conditions where time is of the essence comprising in combination:

(a) pressurized parenteral fluid supply means for rapidly infusing a massive amount of parenteral fluid into a patient;

(b) means for warming the massive amount of parenteral fluid prior to the infusion of said fluid into the patient;

(c) means for controlling the temperature of the parenteral fluid;

(d) means for controlling the rate of discharge of the parenteral fluid; and (e) means for purging air from the parenteral fluid supply means to prevent injury to the patient by an air embolism.

29. Apparatus for the rapid warming and infusion of massive amounts of a parenteral fluid into a patient under conditions where time is of the essence comprising in combination:

(a) pressurized parenteral fluid supply means for rapidly infusing a massive amount of parenteral fluid into a patient;

(b) means for warming the massive amount of parenteral fluid prior to the infusion of said fluid into the patient;

(c) means for controlling the temperature of the parenteral fluid;

(d) means for controlling the rate of discharge of the parenteral fluid; and (e) means for warning when the temperature of the parenteral fluid warming means is above a predetermined value.

30. Apparatus for the rapid warming and infusion of massive amounts of a parenteral fluid into a patient under conditions where time is of the essence comprising in combination:
- (a) pressurized parenteral fluid supply means for rapidly infusing a massive amount of parenteral fluid into a patient;
- (b) means for warming the massive amount of parenteral fluid prior to the infusion of said fluid into the patient;
- (c) means for controlling the temperature of the parenteral fluid;
- (d) means for controlling the rate of discharge of the parenteral fluid; and
- (e) means for warning when the temperature of the parenteral fluid warming means is below a pre-determined value.

31. Apparatus for the rapid warming and infusion of massive amounts of a parenteral fluid into a patient under conditions where time is of the essence comprising in combination:
- (a) pressurized parenteral fluid supply means for rapidly infusing a massive amount of parenteral fluid into a patient;
- (b) means for warming the massive amount of parenteral fluid prior to the infusion of said fluid into the patient;
- (c) means for controlling the temperature of the parenteral fluid;
- (d) means for controlling the rate of discharge of the parenteral fluid; and
- (e) means for warning when the pressure of the pressurized parenteral fluid supply means is below a pre-determined value.

32. Apparatus for the rapid warming and infusion of massive amounts of a parenteral fluid into a patient under conditions where time is of the essence comprising in combination:
- (a) pressurized parenteral fluid supply means for rapidly infusing a massive amount of parenteral fluid into a patient;
- (b) means for warming the massive amount of parenteral fluid prior to the infusion of said fluid into the patient;
- (c) means for controlling the temperature of the parenteral fluid;
- (d) means for controlling the rate of discharge of the parenteral fluid; and
- (e) a primary heating element for maintaining the parenteral fluid warming means in a stand-by condition and a secondary heating element for maintaining the parenteral fluid warming means at the pre-determined temperature during the infusion of the parenteral fluid into the patient.

33. Portable apparatus for the rapid warming and infusion of massive amounts of a parenteral fluid into a patient under conditions where time is of the essence comprising in combination:
- (a) primary heating means for maintaining the apparatus in a stand-by condition such that the parenteral fluid is immediately warmed to a first pre-determined temperature when said apparatus is initially applied for infusing the parenteral fluid into a patient;
- (b) secondary heating means for maintaining the parenteral fluid at the first pre-determined temperature during the infusion of the parenteral fluid into the patient;
- (c) means for warning when the temperature of the parenteral fluid warming means is above a second pre-determined value; and
- (d) means for warning when the temperature of the parenteral fluid warming means is below a third pre-determined value.

34. Apparatus for the rapid warming and infusion of massive amounts of a parenteral fluid into a patient under conditions where time is of the essence comprising in combination:
- (a) a cabinet adapted for mounting a means for rapidly infusing a massive amount of parenteral fluid into a patient means for warming the massive amount of parenteral fluid prior to the infusion of said fluid into the patient;
- (b) pressurized parenteral fluid supply means mounted on said cabinet for rapidly infusing a massive amount of parenteral fluid into a patient;
- (c) means mounted on said cabinet for warming the massive amount of parenteral fluid prior to the infusion of said fluid into the patient;
- (d) means for warning when the temperature of the parenteral fluid warming means is above a second pre-determined value;
- (e) means for warning when the temperature of the parental fluid warming means is below a third pre-determined value; and
- (f) means for warning when the pressure of the pressurized parenteral fluid supply means is below a pre-determined value.

* * * * *